(12) United States Patent
Kayyali

(10) Patent No.: US 9,309,286 B2
(45) Date of Patent: Apr. 12, 2016

(54) COMPOSITIONS AND METHODS FOR AUGMENTING PERMEABILITY BARRIERS

(75) Inventor: Usamah S. Kayyali, Belmont, MA (US)

(73) Assignee: TUFTS MEDICAL CENTER, Boston, MA (US)

( * ) Notice: Subject to any disclaimer, the term of this patent is extended or adjusted under 35 U.S.C. 154(b) by 0 days.

(21) Appl. No.: 14/239,059

(22) PCT Filed: Aug. 16, 2012

(86) PCT No.: PCT/US2012/051051
§ 371 (c)(1),
(2), (4) Date: May 28, 2014

(87) PCT Pub. No.: WO2013/025861
PCT Pub. Date: Feb. 21, 2013

(65) Prior Publication Data
US 2014/0256614 A1 Sep. 11, 2014

Related U.S. Application Data

(60) Provisional application No. 61/524,537, filed on Aug. 17, 2011.

(51) Int. Cl.
| | | |
|---|---|---|
| *C07K 7/08* | (2006.01) | |
| *C07K 7/06* | (2006.01) | |
| *C12N 9/12* | (2006.01) | |
| *C12Q 1/48* | (2006.01) | |
| *G01N 33/50* | (2006.01) | |
| *C07K 16/18* | (2006.01) | |

(52) U.S. Cl.
CPC ... *C07K 7/08* (2013.01); *C07K 7/06* (2013.01); *C07K 16/18* (2013.01); *C12N 9/12* (2013.01); *C12Q 1/485* (2013.01); *G01N 33/5088* (2013.01); *C07K 2317/40* (2013.01); *C07K 2319/10* (2013.01); *C07K 2319/70* (2013.01); *G01N 2800/12* (2013.01)

(58) Field of Classification Search
CPC ............ C07K 7/06; C07K 7/08; C07K 16/18; C07K 2317/40; C07K 2319/10; C07K 2319/70; C12N 9/12; C12Q 1/485; G01N 2800/12; G01N 33/5088
See application file for complete search history.

(56) References Cited

U.S. PATENT DOCUMENTS

2009/0325871 A1   12/2009   Kayyali
2011/0052658 A1   3/2011    Panitch et al.

FOREIGN PATENT DOCUMENTS

WO   WO 2007103543 A2 *   9/2007   ............ A61K 38/12

OTHER PUBLICATIONS

Deron J. Tessier, Transduction of peptide analogs of the small heat shock-related protein HSP20 inhibits intimal hyperplasia, Journal of Vascular Surgery, vol. 40, No. 1, 2004, pp. 106-114.*
Michelle Becker-Hapak, TAT-Mediated Protein Transduction into Mammalian Cells, Methods 24, 247-256 (2001).*
Marian P. Brennan, Peptide Diversity in Drug Discovery, Frontiers in Drug Design & Discovery, 2007, 3, pp. 1-38.*
During et al., "Anthrax lethal toxin paralyzes actin-based motility by blocking Hsp27 phosphorylation." EMBO J. May 2, 2007; 26(9):2240-50.
Goldberg et al., "p38 MAPK activation by TGF-beta1 increases MLC phosphorylation and endothelial monolayer permeability." Am J Physiol Lung Cell Mol Physiol. Jan. 2002; 282(1):L146-54.
Lee et al., "Transforming growth factor-beta1 effects on endothelial monolayer permeability involve focal adhesion kinase/Src." Am J Respir Cell Mol Biol. Oct. 2007; 37(4):485-93.
Liu et al., "Lack of MK2 inhibits myofibroblast formation and exacerbates pulmonary fibrosis." Am J Respir Cell Mol Biol. Nov. 2007; 37(5):507-17.
Liu et al., "Modulation of HSP27 alters hypoxia-induced endothelial permeability and related signaling pathways." J Cell Physiol. Sep. 2009; 220(3):600-10.
Liu et al., "Regulation of vimentin intermediate filaments in endothelial cells by hypoxia." Am J Physiol Cell Physiol. Aug. 2010; 299(2):C363-73.
Lu et al., "Transforming growth factor-beta1-induced endothelial barrier dysfunction involves Smad2-dependent p38 activation and subsequent RhoA activation." J Appl Physiol (1985). Aug. 2006; 101(2):375-84.
McCormick & Ganem, "Phosphorylation and function of the kaposin B direct repeats of Kaposi's sarcoma-associated herpesvirus." J Virol. Jun. 2006; 80(12):6165-70.
McCormick & Ganem, "The kaposin B protein of KSHV activates the p38/MK2 pathway and stabilizes cytokine mRNAs." Science. Feb. 4, 2005; 307(5710):739-41.
Nye et al., "Rat survival to anthrax lethal toxin is likely controlled by a single gene." Pharmacogenomics J. Feb. 2008; 8(1):16-22.
Tessier et al., "Transduction of peptide analogs of the small heat shock-related protein HSP20 inhibits intimal hyperplasia." J Vasc Surg. Jul. 2004; 40(1):106-14.
Warfel et al., "Anthrax lethal toxin induces endothelial barrier dysfunction." Am J Pathol. Jun. 2005; 166(6):1871-81.

* cited by examiner

*Primary Examiner* — James H Alstrum Acevedo
*Assistant Examiner* — Erinne Dabkowski
(74) *Attorney, Agent, or Firm* — Casimir Jones, S.C.; David Casimir; Tanya Arenson

(57) ABSTRACT

Compositions and methods for activating MK2, augmenting permeability barriers, such as epithelial and/or endothelial barriers, and treating diseases, conditions, disorders, and/or injuries associated therewith, such as pulmonary edema and other lung diseases and injuries are provided herein.

12 Claims, 10 Drawing Sheets

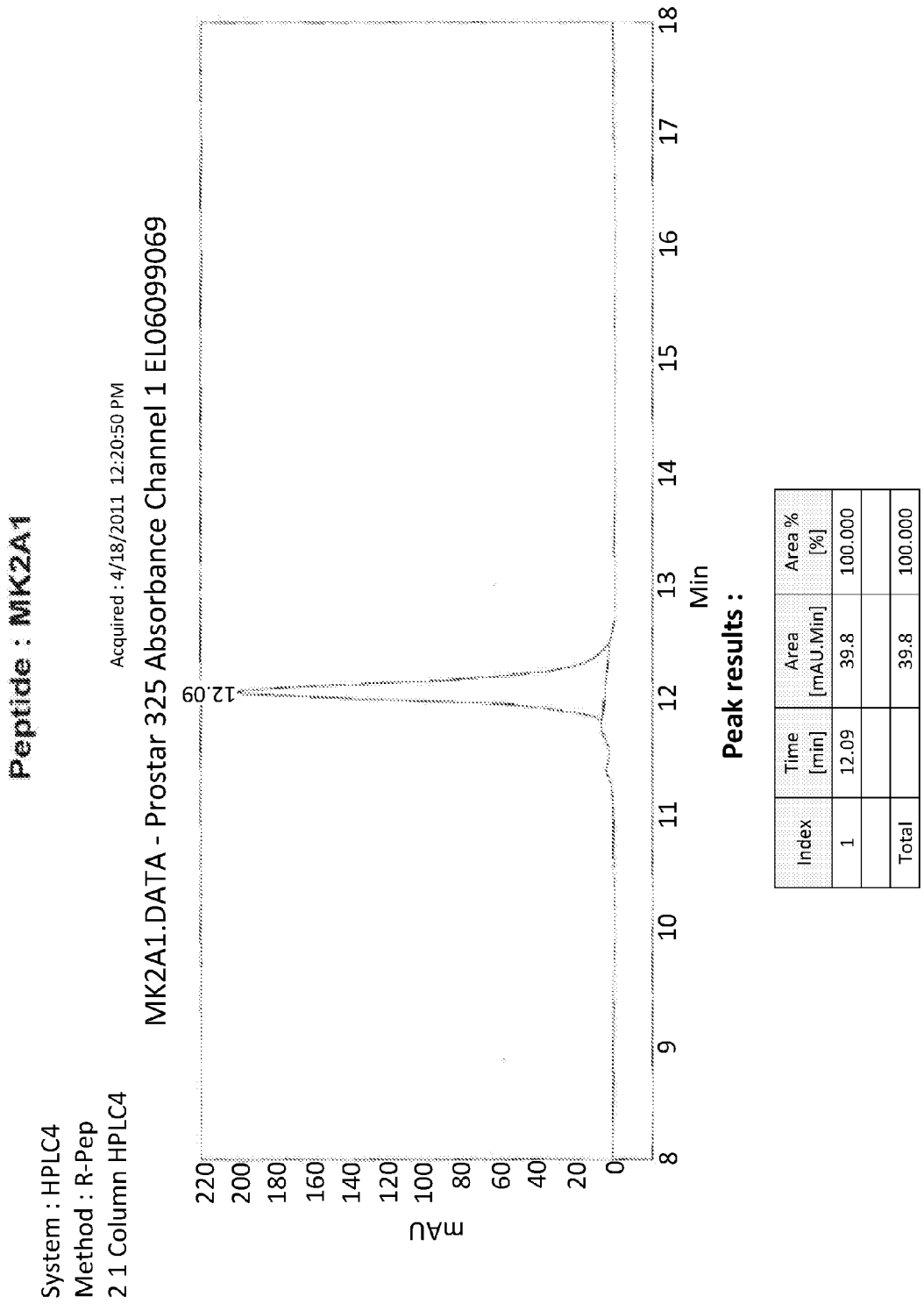

SEQUENCE LISTING

```
<160> NUMBER OF SEQ ID NOS: 13

<210> SEQ ID NO 1
<211> LENGTH: 19
<212> TYPE: PRT
```

```
<213> ORGANISM: Artificial Sequence
<220> FEATURE:
<223> OTHER INFORMATION: Synthetic

<400> SEQUENCE: 1

His Pro Arg Asn Pro Ala Arg Arg Thr Pro Gly Thr Arg Arg Gly Ala
1               5                   10                  15

Pro Ala Ala

<210> SEQ ID NO 2
<211> LENGTH: 11
<212> TYPE: PRT
<213> ORGANISM: Artificial Sequence
<220> FEATURE:
<223> OTHER INFORMATION: Synthetic

<400> SEQUENCE: 2

Tyr Ala Arg Ala Ala Ala Arg Gln Ala Arg Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Tyr Ala Arg Lys Ala Arg Arg Gln Ala Arg Arg
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Tyr Gly Arg Lys Lys Arg Arg Gln Arg
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Tyr Gly Arg Lys Lys Arg Arg Gln Arg Arg Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Gly Arg Lys Lys Arg Arg Gln Arg Arg Arg Pro Pro Gln Cys
1               5                   10

<210> SEQ ID NO 7
<211> LENGTH: 9
```

```
<212> TYPE: PRT
<213> ORGANISM: Artificial Sequence
<220> FEATURE:
<223> OTHER INFORMATION: Synthetic

<400> SEQUENCE: 7

Arg Arg Arg Arg Arg Arg Arg Arg Arg
1               5

<210> SEQ ID NO 8
<211> LENGTH: 30
<212> TYPE: PRT
<213> ORGANISM: Artificial Sequence
<220> FEATURE:
<223> OTHER INFORMATION: Synthetic

<400> SEQUENCE: 8

Tyr Ala Arg Ala Ala Ala Arg Gln Ala Arg Ala His Pro Arg Asn Pro
1               5                   10                  15

Ala Arg Arg Thr Pro Gly Thr Arg Arg Gly Ala Pro Ala Ala
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Synthetic

<400> SEQUENCE: 9

Tyr Ala Arg Lys Ala Arg Arg Gln Ala Arg Arg His Pro Arg Asn Pro
1               5                   10                  15

Ala Arg Arg Thr Pro Gly Thr Arg Arg Gly Ala Pro Ala Ala
            20                  25                  30

<210> SEQ ID NO 10
<211> LENGTH: 28
<212> TYPE: PRT
<213> ORGANISM: Artificial Sequence
<220> FEATURE:
<223> OTHER INFORMATION: Synthetic

<400> SEQUENCE: 10

Tyr Gly Arg Lys Lys Arg Arg Gln Arg His Pro Arg Asn Pro Ala Arg
1               5                   10                  15

Arg Thr Pro Gly Thr Arg Arg Gly Ala Pro Ala Ala
            20                  25

<210> SEQ ID NO 11
<211> LENGTH: 30
<212> TYPE: PRT
<213> ORGANISM: Artificial Sequence
<220> FEATURE:
<223> OTHER INFORMATION: Synthetic

<400> SEQUENCE: 11

Tyr Gly Arg Lys Lys Arg Arg Gln Arg Arg His Pro Arg Asn Pro
1               5                   10                  15

Ala Arg Arg Thr Pro Gly Thr Arg Arg Gly Ala Pro Ala Ala
            20                  25                  30

<210> SEQ ID NO 12
<211> LENGTH: 33
<212> TYPE: PRT
<213> ORGANISM: Artificial Sequence
```

```
<220> FEATURE:
<223> OTHER INFORMATION: Synthetic

<400> SEQUENCE: 12

Gly Arg Lys Lys Arg Arg Gln Arg Arg Pro Pro Gln Cys His Pro
1               5                   10                  15

Arg Asn Pro Ala Arg Arg Thr Pro Gly Thr Arg Arg Gly Ala Pro Ala
                20                  25                  30

Ala

<210> SEQ ID NO 13
<211> LENGTH: 28
<212> TYPE: PRT
<213> ORGANISM: Artificial Sequence
<220> FEATURE:
<223> OTHER INFORMATION: Synthetic

<400> SEQUENCE: 13

Arg Arg Arg Arg Arg Arg Arg Arg His Pro Arg Asn Pro Ala Arg
1               5                   10                  15

Arg Thr Pro Gly Thr Arg Arg Gly Ala Pro Ala Ala
                20                  25
```

COMPOSITIONS AND METHODS FOR AUGMENTING PERMEABILITY BARRIERS

CROSS REFERENCE TO RELATED APPLICATIONS

This present invention is a national phase application under 35 U.S.C. §371 of PCT International Application No. PCT/US2012/051051, filed Aug. 16, 2012, which claims priority to U.S. Provisional Patent Application Ser. No. 61/524,537, filed Aug. 17, 2011, each of which are hereby incorporated by reference in its entirety.

STATEMENT REGARDING FEDERALLY SPONSORED RESEARCH OR DEVELOPMENT

The present disclosure was supported by government funds under 5R01L079320-04 and 1R21AI096087-01 awarded by the National Institutes of Health and the government may have certain rights therein.

FIELD

The present disclosure provides compounds, compositions and methods for activating MK2, augmenting permeability barriers, such as epithelial and/or endothelial barriers (reducing leak), and/or treating diseases, conditions, disorders, and/or injuries associated therewith, such as edema and other barrier diseases and injuries.

BACKGROUND

Endothelial cells that line blood vessels pose a barrier to the flow of fluids and blood components to tissues. Different vascular beds have endothelial barriers of varying permeability. Generally microvascular endothelial cells form tighter barriers than macrovascular endothelial cells, which line large vessels that have multiple layers of cells. Vascular leak and edema usually arise when the microvascular endothelial barrier is compromised. While edema can be tolerated in certain peripheral tissues it can be fatal in the brain or the lung where it can increase intracranial pressure in the former and interfere with gas exchange in the latter.

Microvascular endothelial cells open and close the permeability barrier in response to permeability inducing stimuli. One stimulus which has been shown to cause permeability in both the brain microvasculature (BBB) and the pulmonary microvasculature is hypoxia, which can result in acute mountain sickness (AMS).

AMS is characterized by fatigue and headache which is poorly understood but shown to be related to the low oxygen concentration (hypoxia) at altitude. Mild AMS lies at one end of a spectrum that proceeds to the other end delineated by the often fatal high altitude cerebral edema (HACE). Another related and severe consequence of rapid ascent to altitude is high altitude pulmonary edema (HAPE). Even milder symptoms of AMS have been associated with altered vascular permeability which can also be observed in the face, hands, or feet (Schoene, Chest, 2008, 134, 402-416). High altitude-related vascular leak which seems to occur in different systems is not explainable by blood pressure changes (Lewis et al., Eur. J. Clin. Invest., 1997, 27, 64-68).

Several studies have reported increased permeability in the brain, lung or cultured endothelial monolayers in response to hypoxia (Ali et al., Am. J. Physiol., 1999, 277, L1057-1065; Allen et al., Stroke, 2010, 41, 2056-2063; Baudry et al., Am. J. Respir. Crit. Care Med., 1998, 158, 477-483; Carpenter et al., J. Appl. Physiol., 1998, 84, 1048-1054; Carpenter et al., Am. J. Physiol. Lung Cell. Mol. Physiol., 2001, 281, L941-948; Hansen et al., Scand. J. Clin. Lab. Invest., 1996, 56, 367-372; Hassoun et al., Am. J. Respir. Crit. Care Med., 1998, 158, 299-305; Lewis et al., Eur. J. Clin. Invest., 1997, 27, 64-68; Morocz et al., Exp. Neurol., 2001, 168, 96-104; Ogawa et al., J. Clin. Invest., 1990, 85, 1090-1098; Ogawa et al., Am. J. Physiol., 1992, 262, C546-554; Ogawa et al., Adv. Exp. Med. Biol., 1990, 281, 303-312; Partridge, Am. J. Physiol., 1995, 269, L52-58; Pinsky et al., Semin Cell. Biol., 1995, 6, 283-294; Stelzner et al., J. Clin. Invest., 1988, 82, 1840-1847; and Wojciak-Stothard et al., Am. J. Physiol. Lung Cell. Mol. Physiol., 2006, 290, L1173-1182). Fluid and macromolecules cross endothelial barriers either through the cells (transcellular route), or through gaps between these cells (paracellular route). The latter route is believed to be the major contributor to tissue edema (Dudek et al., J. Appl. Physiol., 2001, 91, 1487-1500). Gap formation between cells which determines paracellular permeability is generally believed to be regulated by contractile forces from within the cell counterbalanced by adhesive forces between cells and between cells and the extracellular matrix (Dudek et al., J. Appl. Physiol., 2001, 91, 1487-1500). The changes in biomechanical forces are dynamic. In healthy normally functioning endothelial layers and in response to physiological stimuli, gaps form transiently and their decrease correlates with barrier augmentation and decreased permeability.

In endothelial cells, hypoxia causes activation of the ROCK-MLCP-MLC2 pathway leading to increased permeability. Hypoxia also causes activation of the p38-MK2-HSP27 pathway which correlates with decreased permeability. The increased contractility of cells is generally believed to be due to interaction of actin filaments with myosin. This process has been shown to be regulated by myosin light chain (MLC2) phosphorylation (Garcia et al., J. Cell. Physiol., 1995, 163, 510-522), which in turn is regulated by kinases and phosphatases, such as myosin light chain phosphatase (MLCP). The increased phosphorylation of MLC2 and ensuing contraction of endothelial cells promote formation of gaps between endothelial cells and increase permeability. Stimuli that weaken the endothelial barrier, e.g., sodium fluoride, act through Rho-activated kinase (ROCK) (Wang et al., Am. J. Physiol. Lung Cell. Mol. Physiol., 2001, 281, L1472-1483). ROCK increases MLC2 phosphorylation through phosphorylating MYPT1, a subunit of MLCP leading to the latter's inhibition (Essler et al., J. Biol. Chem., 1998, 273, 21867-21874; and Robertson et al., Br. J. Pharmacol., 2000, 131, 5-9). MLC2 phosphorylation has been correlated with increased endothelial permeability in response to a variety of agents and stresses including hypoxia. ROCK has been proposed to mediate hypoxia-induced smooth muscle contraction via phosphorylating MYPT1 (Wang et al., Am. J. Respir. Cell. Mol. Biol., 2001, 25, 628-635; and Wang et al., Am. J. Respir. Cell. Mol. Biol., 2003, 24, 24). Another report on porcine pulmonary artery endothelial cells suggested that hypoxia induced Rho activation mediates increased barrier permeability (Wojciak-Stothard et al., Am. J. Physiol. Lung Cell. Mol. Physiol., 2005, 288, L749-760). Recently, hypoxia-induced brain endothelial barrier dysfunction has been linked to activation of Rho and ROCK (Allen et al., Stroke, 2010, 41, 2056-2063) Inhibition of ROCK blocks hypoxia-induced permeability of endothelial monolayers (Liu et al., J. Cell. Physiol., 2009, 220, 600-610). Hypoxia and TGFβ increase the phosphorylation of MYPT1 and MLC2 in rat pulmonary endothelial cells (RPMEC) (Liu et al., J. Cell. Physiol., 2009, 220, 600-610). These results describe that hypoxia increases endothelial barrier permeability through activating ROCK-MLCP-MLC2 signaling and endothelial contractility (Liu et al., J. Cell. Physiol., 2009, 220, 600-610). Furthermore, hypoxia causes a transient increase in endothelial cell contractility that can be blocked by inhibiting ROCK, but not by inhibiting p38 (An et al., Am. J. Physiol. Cell. Physiol., 2005, 289, C521-530).

One of the most commonly reported effects related to increased permeability is increased actin stress fiber formation, typically associated with contractility. Several agents that induce endothelial permeability, e.g., thrombin and $H_2O_2$, have been associated with increased actin stress fiber formation. Hypoxia can induce actin stress fiber formation in RPMEC via activation of p38 and MK2 and phosphorylation of HSP27 (Kayyali et al., J. Biol. Chem., 2002, 277, 42596-42602). However, recent research suggests that instead of being associated with increased permeability, this actin stress fiber formation is actually associated with decreased permeability and a stronger barrier (Liu et al., J. Cell. Physiol., 2009, 220, 600-610).

p38 MAP kinase is implicated in stress response, and when activated by hypoxia, it phosphorylates and activates the kinase MK2, which then phosphorylates the small heat shock protein HSP27 leading to actin filament formation in endothelial cells (An et al., Am. J. Physiol. Cell. Physiol., 2005, 289, C521-530; and Kayyali et al., J. Biol. Chem., 2002, 277, 42596-42602). Unphosphorylated HSP27 binds actin and blocks its polymerization, and has been associated with decreased actin stress fibers and decreased focal adhesions (Schneider et al., J. Cell. Physiol., 1998, 177, 575-584).

Consistent with the role of HSP27 phosphorylation in mediating hypoxia-induced stress fibers, RPMECs that are stably transfected with phospho-mimicking (pm) HSP27 contain significantly more actin stress fibers than mock-transfected RPMEC, a phenotype that could be rescued by siRNA against the pmHSP27 (Kayyali et al., J. Biol. Chem., 2002, 277, 42596-42602; and Liu et al., J. Cell. Physiol., 2009, 220, 600-610). Furthermore, the RPMEC transfected with pmHSP27 form a tighter permeability barrier than wild type RPMEC (Liu et al., J. Cell. Physiol., 2009, 220, 600-610).

Inhibiting the actin stress fibers in pmHSP27 overexpressing cells with cytochalasin D abolished the reduced monolayer intercellular gaps and permeability (Liu et al., J. Cell. Physiol., 2009, 220, 600-610). Increased contractility is dissociated from p38-MK2-HSP27-mediated stress fiber formation which instead is associated with increased cell adhesiveness (An et al., Am. J. Physiol. Cell. Physiol., 2005, 289, C521-530).

Increased understanding of signaling pathways in normal physiology and disease led to numerous new drug candidates that target these signaling pathways. The majority of these drug candidates are designed to be inhibitors of enzymes, such as kinases, because they are easier to develop based on better knowledge of the structure of active sites or substrate binding sites. For example, inhibitors of p38 have been developed by several drug companies to target inflammation and other processes. These inhibitors have not moved to the clinic as fast as anticipated because of their toxicity. Indeed, one major toxicity associated with p38 inhibitors is related to intestinal epithelial permeability barrier compromise (Morris et al., Toxicol. Pathol., 2010, 38, 606-618). The fact that MK2 inhibitors caused a similar type of toxicity indicates that the effects on epithelial barrier function might be due to a role for p38-MK2 signaling in proper barrier function (Morris et al., Toxicol. Pathol., 2010, 38, 606-618).

MK2 is the immediate kinase that phosphorylates HSP27. Elucidation of the structure of MK2 revealed that it contains an autoinhibitory domain. This domain was reported to be a target of Kaposin (Kaposin proposed to bind to and block the region of MK2 where the autoinhibitory domain binds), the product of the HSV virus that causes Kaposi's sarcoma (McCormick et al., Science, 2005, 307, 739-741; and McCormick et al., J. Virol., 2006, 80, 6165-6170).

Transduction domains have been reported to increase the penetration of peptides into cells. One sequence with demonstrated effectiveness has been identified (Tessier et al., J. Vasc. Surg., 2004, 40, 106-114).

Pulmonary edema is a condition caused by excess fluid in the lungs. This fluid collects in the numerous air sacs in the lungs, making it difficult to breathe. In most cases, heart problems cause pulmonary edema. Fluid can accumulate for other reasons, however, including pneumonia, exposure to certain toxins or infections, adverse reaction to medications, severe injuries (trauma), systemic infection (sepsis), pneumonia and shock, and exercising or living at high elevations. Depending on the cause, pulmonary edema symptoms may appear suddenly or develop slowly.

Treatments include morphine (Astramorph, Roxanol), afterload reducers (e.g., nitroprusside (Nitropress), enalapril (Vasotec) and captopril (Capoten), and blood pressure medications. Pulmonary edema can be fatal, even if treated.

Additional treatments for augmenting permeability barriers and treating diseases, conditions, disorders, and/or injuries associated therewith, such as pulmonary edema and other lung diseases and injuries are needed.

SUMMARY

The present disclosure provides peptides comprising a transduction domain and a domain that blocks an autoinhibitory domain of MK2. In some embodiments, the carboxy-terminus of the transduction domain is linked to the amino-terminus of the domain that blocks an autoinhibitory domain of MK2. In some embodiments, the link between the transduction domain and the domain that blocks an autoinhibitory domain of MK2 is a peptide bond. In some embodiments, the transduction domain comprises an amino acid sequence that is at least 70% identical to YARAAARQARA (SEQ ID NO:2), YARKARRQARR (SEQ ID NO:3), YGRKKRRQR (SEQ ID NO:4), YGRKKRRQRRR (SEQ ID NO:5), GRKKRRQRRRPPQC (SEQ ID NO:6), or RRRRRRRRR (SEQ ID NO:7). In some embodiments, the domain that blocks an autoinhibitory domain of MK2 comprises an amino acid sequence that is at least 70% identical to HPRNPARRT-PGTRRGAPAA (SEQ ID NO:1). In some embodiments, the peptide comprises an amino acid sequence that is at least 70% identical to YARAAARQARAHPRNPARRTPGTRRGA-PAA (SEQ ID NO:8), YARKARRQARRHPRNPARRT-PGTRRGAPAA (SEQ ID NO:9), YGRKKRRQRHPRN-PARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTR-RGAPAA (SEQ ID NO:12), or RRRRRRRRHPRNPAR-RTPGTRRGAPAA (SEQ ID NO:13). In some embodiments, the peptide comprises an amino acid sequence which is YARAAARQARAHPRNPARRTPGTRRGAPAA (SEQ ID NO:8), YARKARRQARRHPRNPARRTPGTRRGAPAA (SEQ ID NO:9), YGRKKRRQRHPRNPARRTPGTRRGA-PAA (SEQ ID NO:10), YGRKKRRQRRRHPRNPARRT-PGTRRGAPAA (SEQ ID NO:11), GRKKRRQRRRP-PQCHPRNPARRTPGTRRGAPAA (SEQ ID NO:12), or RRRRRRRRHPRNPARRTPGTRRGAPAA (SEQ ID NO:13). In some embodiments, at least one L-amino acid is replaced with a D-amino acid. In some embodiments, the peptide is cyclized.

The present disclosure also provides pharmaceutical compositions comprising at least one peptide described herein and a pharmaceutically acceptable carrier or diluent. In some embodiments, the pharmaceutical composition further comprises at least one preload reducer, morphine, afterload reducer, blood pressure medication, or acetazolamide (for acute lung injury peptide plus antibiotic).

The present disclosure also provides methods of activating MK2 in a subject comprising administering to the subject a peptide described herein or a composition comprising the same.

The present disclosure also provides methods of augmenting the permeability barrier (reducing leak) in a subject comprising administering to the subject a peptide described herein or a composition comprising the same.

The present disclosure also provides methods of treating a subject having a disease, condition, disorder, or injury associated with an epithelial and/or an endothelial barrier comprising administering to a subject a peptide described herein or a composition comprising the same. In some embodiments, the disease, condition, disorder, or injury associated with an epithelial and/or an endothelial barrier is an edema, a wound, a lung disease, chronic fatigue syndrome, acute mountain sickness (AMS), high altitude-related vascular leak, or caused by a pathogen. In some embodiments, the edema is a pulmonary edema or cerebral edema. In some embodiments, the edema is high altitude pulmonary edema (HAPE) or high altitude cerebral edema (HACE). In some embodiments, the pathogen is the H1N1 flu virus or the Hanta virus. In some embodiments, the lung disease is pulmonary fibrosis.

Diseases, conditions, disorders, or injuries that affect the endothelial permeability barrier include those that affect the pulmonary endothelial permeability barrier, and include: 1) acute lung injury/acute respiratory distress syndrome (ALI/ARDS). ALI is associated with over 60 causes that can benefit from treatment including sepsis, influenza, pneumonia, trauma, anthrax; and 2) pulmonary edema due to other causes such as acute mountain sickness (AMS) or high altitude pulmonary edema (HAPE), or other causes of hypoxia.

Diseases, conditions, disorders, or injuries that affect the endothelial permeability barrier include those that affect the brain endothelial barrier/blood brain barrier (BBB), and include: 1) brain edema due to altitude, AMS, or high altitude cerebral edema (HACE), or other cause of hypoxia; and 2) brain edema due to other causes, poisoning or disease, e.g., chronic fatigue syndrome.

Diseases, conditions, disorders, or injuries that affect the endothelial permeability barrier include those that affect other microvascular barriers, and include: edema and infiltration in other tissues, e.g., peripheral edema, facial edema or pericardial edema.

Diseases, conditions, disorders, or injuries that affect the endothelial permeability barrier include those that affect macrovascular beds leading to diseases of the vascular wall, and include: 1) pulmonary hypertension; 2) systemic hypertension; 3) atherosclerosis; and 4) aneurysms.

Diseases, conditions, disorders, or injuries that affect the epithelial permeability barrier include: 1) diseases that affect the intestinal epithelial barrier such as inflammatory bowel disease (IBD); 2) diseases that affect the lung epithelial barrier, pneumonia, lung injury, COPD; 3) diseases that affect the kidney epithelial barrier; and 4) diseases that affect other epithelial barriers.

Diseases, conditions, disorders, or injuries that involve remodeling fibrosis, scarring and abnormal wound healing include: 1) pulmonary fibrosis; 2) renal fibrosis; 3) cardiac fibrosis; 4) skin fibrosis; and 5) wound healing (fibroblasts that do not differentiate properly because of lack of MK2 activity proliferate more and produce more collagen resulting in more scarring; blood vessels that form in wound healing are leaky (similar to tumor feeding blood vessels); excessive leakiness results in increased stroma formation and excessive scarring, a process that can be inhibited by the peptides described herein; keratinocytes, macrophages or other factors are affected by MK2.

Diseases, conditions, disorders, or injuries that involve MK2 also include cancers, such as, for example: 1) tumors are often hypoxic and blood vessels that feed tumors are leaky compared to normal blood vessels; this leakiness is believed to be important in development of stroma that promotes tumor growth and also allows cancer cells to enter circulation leading to metastasis; inhibiting leakiness of tumor vessels by the peptides described herein would inhibit the formation of stroma that is enhanced by leak of plasma proteins and fibrin gel formation and other serum factors that stimulate tumor growth, angiogenesis, and further stroma formation; 2) fibroblasts that surround tumors and invasion and metastasis; evidence suggests that fibroblasts that surround early tumor formation play a role in invasion and metastasis; undifferentiated fibroblasts might be the ones that are more proliferative; treatment with the peptides described herein may differentiate fibroblasts into myofibroblasts and limit tumor invasion and metastasis.

The present disclosure also provides methods of detecting MK2 activity in a cell comprising: contacting the cell with anthrax toxin; contacting the cell with a test compound; and detecting the presence of phosphorylated HSP27; wherein a greater amount of phosphorylated HSP27 in the presence of the test compound compared to the amount of phosphorylated HSP27 in the presence of anthrax toxin indicates that the test compound induces MK2 activity in the cell.

The present disclosure also provides methods of detecting a decrease in barrier leak in a mammal in vivo comprising: administering to the mammal a test compound or a control compound; administering to the mammal anthrax toxin; administering to the mammal a test compound or a control compound; administering a detectable reagent to the mammal; and examining lung tissue from the mammal, whereby a decrease in the amount of the detectable reagent in the lung tissue from the mammal receiving the test compound and anthrax toxin compared to the amount of the detectable reagent in the lung tissue from the mammal receiving the anthrax toxin and the control compound, indicates that the test compound decreases barrier leak in a mammal in vivo.

The present disclosure also provides any one or more of the foregoing compounds for use as a medicament.

The present disclosure also provides any one or more of the foregoing compounds for use in activating MK2, augmenting permeability barriers, such as epithelial and/or endothelial barriers, and/or treating diseases, conditions, disorders, and/or injuries associated therewith. In some embodiments, a mammal is administering one or more of the compounds described herein.

The present disclosure also provides uses of any one or more of the foregoing compounds in the manufacture of a medicament for activating MK2, augmenting barrier transport, such as epithelial and/or endothelial barriers, and/or treating diseases, conditions, disorders, and/or injuries associated therewith. In some embodiments, a mammal is administering one or more of the compounds described herein.

The present disclosure also provides any one or more of the foregoing compounds, or pharmaceutical compositions comprising the same, or methods of preparing the same, or methods of using the same, or uses any one or more of the foregoing compounds, substantially as described with reference to the accompanying examples and/or figures.

DETAILED DESCRIPTION

Figure 1:
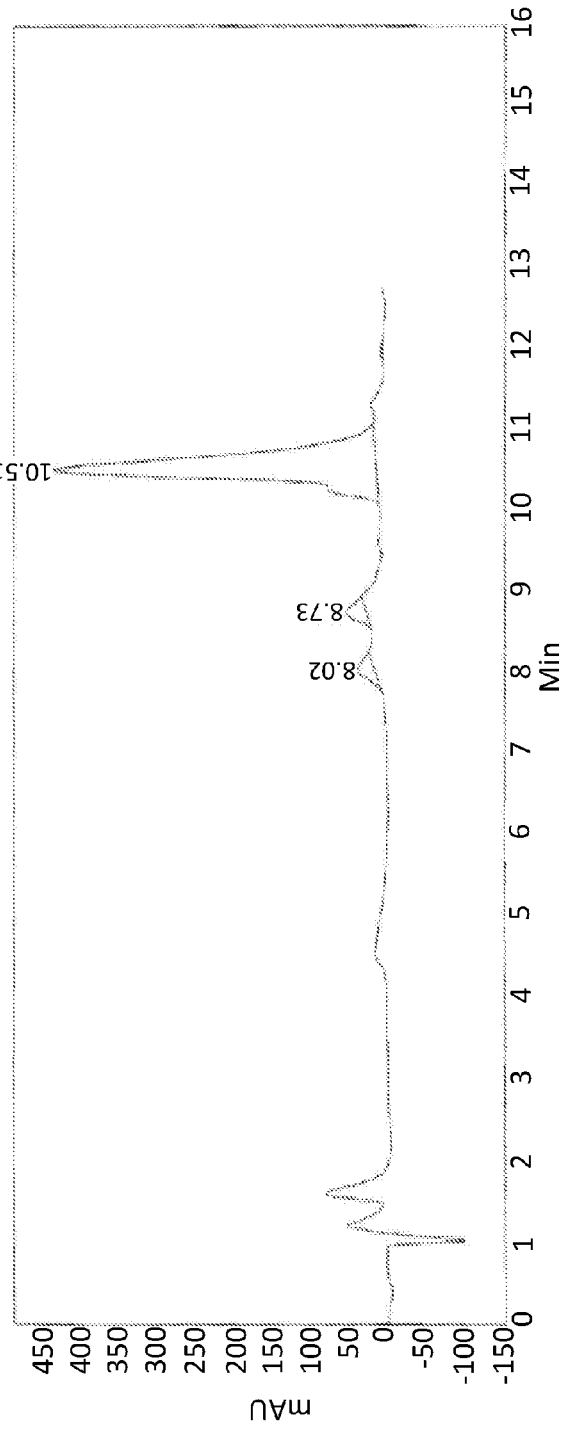
FIG. 1 shows HPLC of peptides of embodiments of the present disclosure.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human or non-human mammal subject.

As used herein, the term "diagnosed," as used herein, refers to the recognition of a disease by its signs and symptoms (e.g., resistance to conventional therapies), or genetic analysis, pathological analysis, histological analysis, and the like.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "effective amount" refers to the amount of a compound (e.g., a compound of the present disclosure) sufficient to effect beneficial or desired results. An effective amount can be administered in one or more administrations, applications or dosages and is not limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy.

Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa., (1975)).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, at least 65% free, at least 70% free, at least 75% free, at least 80% free, at least 85% free, at least 90% free, at least 95% free, at least 96% free, at least 97% free, at least 98% free, at least 99% free, or 100% free from other components with which they usually associated.

As used herein, the term "modulate" refers to the activity of a compound (e.g., a compound of the present disclosure) to affect (e.g., to promote or retard) an aspect of cellular function, including, but not limited to, activation of MK-2 and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., bacterial infection). Test compounds comprise both known and potential therapeutic compounds. A test compound can be determined to be therapeutic by using the screening methods of the present disclosure. A "known therapeutic compound" refers to a therapeutic compound that has been shown (e.g., through animal trials or prior experience with administration to humans) to be effective in such treatment or prevention. In some embodiments, "test compounds" are agents that modulate activation of MK-2.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand"; the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

As used herein, the term "RNA interference" or "RNAi" refers to the silencing or decreasing of gene expression by siRNAs. It is the process of sequence-specific, posttranscriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "augment permeability barriers" means a decrease in permeability to water, fluids, serum proteins (e.g., serum albumin) or other blood components, compound, agent, or drug across any epithelial and/or endothelial barrier in a subject. Exemplary epithelial and/or endothelial barriers include, but are not limited to blood vessels (e.g., arteries, veins, and capillaries) Additional examples of a barrier include, but are not limited to, micro/macro vascular endothelial cells, brain microvasculature such as the blood brain barrier (BBB), and pulmonary microvasculature.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, condition, or injury is prevalent.

The present disclosure provides compounds that activate MK2. In some embodiments, the compound is a peptide. In some embodiments, the compound is a nucleic acid molecule. In some embodiments, the compound is an antibody.

The present disclosure provides peptides that activate MK2. In some embodiments, the peptide comprises a domain that blocks an autoinhibitory domain of MK2 and, optionally, a transduction domain. Transduction domains are sequences of amino acids that have been identified in viral proteins, e.g., HIV Trans-Activator of Transcription (TAT), which enable these proteins to penetrate cells (van den Berg et al., Curr. Opin. Biotechnol., 2011, 22, 888-893). Although the exact mechanism by which they act is not well understood, these sequences are believed to improve cell entry and allow peptides to escape endosomes. In some embodiments, the transduction domain is linked at its carboxy-terminus via an amino acid linkage to the amino-terminus of the domain that blocks an autoinhibitory domain of MK2. Other linkages know to those skilled in the art may also be used.

In some embodiments, the peptide that activates MK2 comprises from about 25 to about 50 amino acids, from about 25 to about 45 amino acids, from about 25 to about 40 amino acids, or from about 25 to about 35 amino acids. In some embodiments, the peptide that activates MK2 comprises from about 25 to about 40 amino acids, from about 26 to about 38 amino acids, from about 27 to about 36 amino acids, or from about 28 to about 33 amino acids.

In some embodiments, the domain that blocks an autoinhibitory domain of MK2 comprises HPRNPARRTPGTRRGAPAA (SEQ ID NO:1), or an amino acid sequence that is at least 70%, at least 75%, at least 80%, at least 85%, at least 90%, or at least 95% identical thereto.

In some embodiments, the transduction domain comprises YARAAARQARA (SEQ ID NO:2), YARKARRQARR (SEQ ID NO:3), YGRKKRRQR (SEQ ID NO:4), YGRKKRRQRRR (SEQ ID NO:5), GRKKRRQRRRPPQC (SEQ ID NO:6), or RRRRRRRRR (SEQ ID NO:7), or an amino acid sequence that is at least 70%, at least 75%, at least 80%, at least 85%, at least 90%, or at least 95% identical thereto.

In some embodiments, the peptide that activates MK2 comprises YARAAARQARAHPRNPARRTPGTRRGAPAA (SEQ ID NO:8), YARKARRQARRHPRNPARRTPGTRRGAPAA (SEQ ID NO:9), YGRKKRRQRHPRNPARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTRRGAPAA (SEQ ID NO:12), or RRRRRRRRRHPRNPARRTPGTRRGAPAA (SEQ ID NO:13), or an amino acid sequence that is at least 70%, at least 75%, at least 80%, at least 85%, at least 90%, or at least 95% identical thereto.

Percent sequence identity can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In some embodiments, 1, 2, 3, or 4 amino acids from the domain that blocks an autoinhibitory domain of MK2, or from any of the transduction domains recited herein, or from any of the peptides that activate MK2 recited above may be deleted. In some embodiments, 1, 2, 3, or 4 amino acids may be inserted into the domain that blocks an autoinhibitory domain of MK2, or into any of the transduction domains recited herein, or into any of the peptides that activate MK2 recited above. In some embodiments, 1, 2, 3, or 4 amino acids within the domain that blocks an autoinhibitory domain of MK2, or within any of the transduction domains recited herein, or within any of the peptides that activate MK2 recited above may be replaced with other amino acids. Suitable amino acid substitutions include conservative amino acid substitutions. For example, individual amino acid substitutions can be selected from any one of the following: 1) the set of amino acids with nonpolar sidechains, for example, Ala, Cys, Ile, Leu, Met, Phe, Pro, Val; 2) the set of amino acids with negatively charged side chains, for example, Asp, Glu; 3) the set of amino acids with positively charged sidechains, for example, Arg, H is, Lys; and 4) the set of amino acids with uncharged polar sidechains, for example, Asn, Cys, Gln, Gly, H is, Met, Phe, Ser, Thr, Trp, Tyr, to which are added Cys, Gly, Met and Phe.

A naturally occurring amino acid can also be replaced with, for example, a non-naturally occurring amino acid such as, for example, norleucine, ornithine, norvaline, homoserine, and other amino acid residue analogues such as those described in Ellman et al., Meth. Enzym., 1991, 202, 301-336. To generate such non-naturally occurring amino acid residues, the procedures of Noren et al., Science, 1989, 244, 182 and Ellman et al., supra, can be used. Briefly, these procedures involve chemically activating a suppressor tRNA with a non-naturally occurring amino acid residue followed by in vitro transcription and translation of the RNA.

The peptides described herein can further be modified. Some modifications may increase the stability and activity of a peptide to enable reduced dosing level or frequency, as well as enable alternative routes of administration, e.g., oral or inhalation. The following are examples of modifications of peptides that may increase stability, activity, specificity, and/or efficacy.

1) Replace labile amino acids with ones that increase stability and improve activity. Such replacement can be performed based upon HPLC analysis of peptide incubation in serum or liver/lung homogenates. For example, lysines and arginines that are recognized by trypsin can be replaced with glutamine.

2) Replace one or more L-amino acids with D-amino acids. D-amino acids are unnatural amino acids which are less likely to be attacked by proteases. For example, a protease cleavage site prediction program has identified 8 cleavage sites for trypsin. To reduce the probability of this proteolysis, one or more L-arginines (R) in the peptide can be replaced with D-arginines as described by Powell et al. (Pharm. Res., 1993, 10, 1268-1273.)

3) Reduce the size of the peptide. Removing non-essential sequences or individual residues may improve entry into target cells. Use of smaller transduction domains, such as those described herein, may be carried out. An example of similar successful manipulation of somastatin is described in Harris (Gut, 1994, 35(3 Suppl), S1-4).

4) Oligomerize the peptide. The peptide molecular weight is less than 5 kDa, and hence is likely to be rapidly excreted through kidneys. Oligomerization may improve bioavailability. Oligomerization can be carried out by synthesizing repeating sequences such as dimers, trimers and polymers to increase the molecular mass so the peptide will be more stable and less easily excreted. These oligomers (n=number of repeats) may consist of repeats of the whole structure, for example, (YARAAARQARAHPRNPARRTPGTRRGA-PAA)n (SEQ ID NO:84. Alternately, only the active sequence can be repeated, for example, YARAAARQARA(HPRN-PARRTPGTRRGAPAA)n (SEQ ID NO:8), and the cell permeation peptide/transduction domain added afterwards at the N-terminus. The oligomers could also be synthesized from recombinant DNA which might be more cost-effective than chemical synthesis of long peptides.

5) Cyclize the peptide. Cyclizing a peptide may protect it against proteolysis and degradation. Cyclizing the peptide head to tail can be accomplished by linking the amino terminus to the carboxy terminus as described by Marastoni et al. (Arzneimittelforschung, 1994, 44, 1073-1076). In addition, cyclizing a peptide may occur via side-chain to side-chain. Further, cyclizing a peptide may occur through commonly used coupling methods using agents such as, for example, p-nitrophenyl esters, the azide method, 2,4,5-trichlorophenyl and pentafluorophenyl esters and the mixed anhydride method. Other more direct methods of activation using N,N-dicyclohexylcarbodiimide (DCC) with catalysts such as HOBt, HONSu, and HOAt are also suitable. Use of use of a water soluble carbodiimide EDC (1-ethyl-3-(3-dimethylaminopropyl)carbodiimide hydrochloride) is also suitable. Suitable successors to the conventional azide coupling includes the use of DPPA and PyBrop. Also included are: 1-benzotriazole-tris-dimethyl aminophosphonium hexafluorophosphate (BOP), O-(benzotriazol-1-yl)-1,1,3,3-tetramethyl uronium hexafluorophosphate (HBTU), 1-benzotriazolyloxy-tris-pyrrolidino-phosphonium hexafluorophosphate (PyBOP), O-(benzotriazol-1-yl)-1,1,3,3-tetramethyl uronium tetrafluoroborate (TBTU), 7-azabenzotriazol-1-yloxytrispyrrolidino phosphonium hexafluorophosphate (PyAOP), O-(7-azabenzotriazol-1-yl)-1,1,3,3-tetramethyl uronium hexafluorophosphate (HATU), 7-azabenzotriazol-1-yloxy-tris-dimethyl aminophosphonium hexafluorophosphate (AOP), O-(7-azabenzotriazol-1-yl)-1,1,3,3-tetramethylene uronium hexafluorophosphate (HAPyU), and O-(7-azabenzotriazol-1-yl)-1,1,3,3-pentamethylene uronium hexafluorophosphate (HAPipU). See, Davies, J. Peptide Science, 2003, 9, 471-501.

6) PEGylate. Adding polyethylene glycol of different sizes, e.g., 40 kDa, to the amino-, carboxy-, and/or inside of the molecule may improve its stability. An example of the latter approach in stabilizing interferon alpha is described by Ramon et al. (Pharm. Res., 2005, 22, 1374-1386).

7) Other modifications: C-terminal amidation or N-terminal acetylation as described in, for example, Brinckerhoff et al. (Int'l J. Cancer, 1999, 83, 326-334), or N-pyroglutamylation as described in, for example, Green et al. (J. Endocrinol., 2004, 180, 379-388). Other examples include conjugation of various fatty acids ranging from 4-18 chain length as described in, for example, DasGupta et al. (Biol. Pharma. Bull., 2002, 25, 29-36).

8) Biodegradable modifications: e.g., polymers of N-acetylneuraminic acid (poysialic acids) as described in, for example, Georgiadis et al. (Cell. Mol. Life. Sci., 2000, 57, 1964-1969).

9) Combination with delivery systems that enable sustained release. Carriers such as liposomes, microspheres or microcapsules, poly lactic acid (PLA), poly lactic/glycolic acid (PLGA) as described in, for example, Heya et al. (J. Pharm. Sci., 1994, 83, 798-801), nanoparticles and emulsions, cyclodextrins and derivatives.

10) Formulations that protect peptides such as those containing different types of protease inhibitors. In addition, formulation containing multifunctional polymers which exhibit mucoadhesive properties as well as enzyme inhibitory activity, e.g., poly(acrylates), thiolated polymers, and polymer-enzyme inhibitor conjugates.

In some embodiments, peptidomimetics of the peptides described herein are provided. The use of peptides as lead compounds, and subsequently conversion into low-molecular-weight nonpeptide molecules (peptidomimetics), have successfully led to development of small-molecule antagonists of intracellular targets (Bottger et al., J. Mol. Biol., 1997, 269, 744-56; Bottger et al., Oncogene, 1996, 13, 2141-7). Therefore, peptidomimetics have emerged as a powerful means for overcoming the obstacles inherent in the physical characteristics of peptides, improving their therapeutic potential (Kieber-Emmons et al., Curr. Opin. Biotechnol., 1997, 8, 435-41; Beeley, Trends Biotechnol., 1994, 12, 213-6; and Moore et al., Trends Pharmacol. Sci., 1994, 15, 124-9). In some embodiments, compared to native peptides, peptidomimetics possess desirable pharmacodynamic properties superior to natural peptides, including good oral activity, long duration of action, better transport through cellular membranes, decreased rate of excretion, and decreased hydrolysis by peptidases.

Development of a small molecule peptidomimetic generally involves identification of the smallest functional peptide unit capable of inhibiting the targeted interaction. A growing body of literature demonstrates that high-affinity ligands can be selected from peptide libraries displayed on bacteriophage (Sulochana et al., Curr. Pharm. Des., 2007, 13, 2074-86; Cwirla et al., Proc. Natl. Acad. Sci. USA, 1990, 87, 6378-82; Scott et al., Science, 1990, 249, 386-90; and Devlin et al., Science, 1990, 249, 404-6), and many applications have been directed toward antagonizing the function of a protein ligand (Dower, Curr. Opin. Chem. Biol., 1998, 2, 328-34; and Sidhu et al., Methods Enzymol., 2000, 328, 333-63). Because the libraries can be very large ($10^{11}$ or more individual members), no initial assumptions are required concerning how to bias the library, nor the selective enrichment of rare binding phage through biological amplification and rescreening. Those sequences that bind can be identified easily by sequencing their encoding DNA.

In some embodiments, peptide ligands such identified further serve as starting points for a combinatorial chemistry approach or a medicinal chemistry-based peptidomimetic approach for the development of new directed therapeutic agents. In addition, the determination of the structural basis for the high-binding affinity of these peptides for their substrate contributes to the rational design of a therapeutic agent.

The present disclosure also provides nucleic acid molecules encoding any of the peptides disclosed herein, vectors comprising any of the nucleic acid molecules disclosed herein, compositions comprising any of the nucleic acid molecules or vectors disclosed herein, as well as host cells comprising any of the nucleic acid molecules or vectors disclosed herein.

The present disclosure also provides nucleic acid molecules that activate MK2. For example, in some embodiments, oligomeric antisense or RNAi compounds, particularly oligonucleotides, can be used to modulating the function of nucleic acid molecules encoding MK2 signaling molecules, ultimately modulating the amount of MK2 expressed.

In some embodiments, RNAi is utilized to activate MK2 by, for example, controlling the expression of MK2 regulators. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl et al., Mol. Intervent., 2002, 2, 158-67).

The transfection of siRNAs into animal cells results in the potent, long-lasting posttranscriptional silencing of specific genes (Caplen et al., Proc. Natl. Acad. Sci. USA, 2001, 98, 9742-7; Elbashir et al., Nature, 2001, 411, 494-8; Elbashir et al., Genes Dev., 2001, 15, 188-200; and Elbashir et al., EMBO J., 2001, 20, 6877-88). Methods and compositions for performing RNAi with siRNAs are described, for example, in U.S. Pat. No. 6,506,559.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al., Science, 2002, 296, 550-3; and Holen et al., Nuc. Acids Res., 2002, 30, 1757-66).

An important factor in the design of siRNAs is the presence of accessible sites for siRNA binding. Bahoia et al., (J. Biol. Chem., 2003, 278, 15991-15997) describe the use of a type of DNA array called a scanning array to find accessible sites in mRNAs for designing effective siRNAs. These arrays comprise oligonucleotides ranging in size from monomers to a certain maximum, usually Corners, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7 mers to 25 mers), where it is important to achieve a compromise between oligonucleotide length and binding affinity, to retain efficacy and target specificity (Sohail et al., Nuc. Acids Res., 2001, 29, 2041-2045). Additional methods and concerns for selecting siRNAs are described for example, in WO 05/054270, WO 05/038054A1, WO 03/070966A2, J. Mol. Biol., 2005, 348, 883-93, J. Mol. Biol., 2005, 348, 871-81, and Nuc. Acids Res., 2003, 31, 4417-24. In addition, software (e.g., the MWG online siMAX siRNA design tool) is commercially or publicly available for use in the selection of siRNAs.

In some embodiments, the present disclosure utilizes siRNA including blunt ends (see, e.g., US 2008-0200420), overhangs (see, e.g., US 2008-0269147A1), locked nucleic acids (see, e.g., WO 08/006,369, WO 08/043,753, and WO 08/051,306). In some embodiments, siRNAs are delivered via gene expression or using bacteria (see, e.g., Xiang et al., Nature, 2006, 24, 6; and WO 06/066048).

In other embodiments, shRNA techniques (see, e.g., US 2008-0025958) are utilized. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA polymerase III.

In some embodiments, MK2 expression is activated using antisense compounds that specifically hybridize with one or more nucleic acids encoding MK2 modulators. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of MK2. In the context of the present disclosure, "modulation" means either an increase (stimulation) or a decrease (inhibition) in the expression of a gene. For example, expression of MK2 may be enhanced.

The present disclosure contemplates the use of any genetic manipulation for use in modulating the expression of MK2. Examples of genetic manipulation include, but are not limited to, gene knockout (e.g., removing an MK2 modulating gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter (e.g., an androgen-responsive promoter)).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Suitable methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are suitable gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908; 6,019,978; 6,001,557; 5,994,132; 5,994,128; 5,994,106; 5,981,225; 5,885,808; 5,872,154; 5,830,730; and 5,824,544.

Vectors may be administered to subjects in a variety of ways. For example, in some embodiments of the present disclosure, vectors are administered into tissue (e.g., lung tissue) using direct injection. In other embodiments, administration is via the blood or lymphatic circulation (see, e.g., PCT publication WO 99/02685). Exemplary dose levels of adenoviral vector are $10^8$ to $10^{11}$ vector particles added to the perfusate.

The present disclosure provides antibodies that activate MK2. In some embodiments, antibodies that target MK2 or MK2 modulators are chosen. Any suitable antibody (e.g., monoclonal, polyclonal, or synthetic) may be utilized in the therapeutic methods disclosed herein. In some embodiments, the antibodies are humanized antibodies. Methods for humanizing antibodies are well known in the art (see, e.g., U.S. Pat. Nos. 6,180,370; 5,585,089; 6,054,297; and 5,565,332). In some embodiments, the antibody is a fragment selected from a single chain antibody (scFv), a $F(ab')_2$ fragment, a Fab fragment, and an Fd fragment.

The present disclosure provides pharmaceutical compositions comprising one or more of the compounds (e.g., peptides, peptidomimetics, nucleic acid molecules, and antibodies described herein, or any mixture thereof) that activate MK2.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, liquid syrups, soft gels, suppositories, and enemas. The compositions may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In some embodiments, the pharmaceutical composition may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

In some embodiments, the pharmaceutical composition contains a) one or more agents described herein that activate MK2, and b) one or more other agents useful in augmenting permeability barriers, such as epithelial and/or endothelial barriers, and/or treating diseases, conditions, disorders, and/or injuries associated therewith, such as edema and other barrier diseases and injuries.

In some embodiments, the compounds (e.g., peptides, peptidomimetics, nucleic acid molecules, and antibodies) described herein are used to activate MK2. In some embodiments, the compounds described herein are used to modulate MK2 modulators that results in the activation of MK2. Thus, the present disclosure provides methods of activating MK2 in a subject, optionally in need thereof, comprising administering to the subject a compound (e.g., peptide, peptidomimetic, nucleic acid molecule, and antibody), or a composition comprising the same, that activates MK2. Activation of MK2 is important for fibroblast differentiation into myofibroblasts, which may be important in limiting fibrosis and scarring and improve tissue repair and wound healing.

In some embodiments, the compounds (e.g., peptides, peptidomimetics, nucleic acid molecules, and antibodies) described herein are used to augment permeability barriers, which reduces permeability and leak, such as epithelial and/or endothelial barriers. In some embodiments, diseases, conditions, disorders, and/or injuries in lung or blood brain barrier function are treated in a subject. Thus, the present disclosure provides methods of augmenting permeability barriers in a subject, optionally in need thereof, comprising administering to the subject a compound (e.g., peptide, peptidomimetic, nucleic acid molecule, and antibody), or a composition comprising the same, that augment permeability barriers.

In some embodiments, the compounds (e.g., peptides, peptidomimetics, nucleic acid molecules, and antibodies) described herein are used to treat diseases, conditions, disorders, and/or injuries associated with MK2 and/or barrier dysfunction, such as epithelial and/or endothelial barriers. Thus, the present disclosure provides methods of treating diseases, conditions, disorders, and/or injuries associated with MK2 and/or barrier dysfunction in a subject, optionally in need thereof, comprising administering to the subject a compound (e.g., peptide, peptidomimetic, nucleic acid molecule, and antibody), or a composition comprising the same. In some embodiments, the subject has an edema, such as pulmonary or cerebral. In some embodiments, the subject has a lung disease. In some embodiments, the subject is in need of decreased permeability of the blood brain or lung barrier, and/or wound healing. Examples of diseases, conditions, disorders, and/or injuries associated with MK2 and/or barrier dysfunction/disruption include, but are not limited to, chronic fatigue syndrome, acute mountain sickness (AMS), high altitude pulmonary edema (HAPE), high altitude cerebral edema (HACE), high altitude-related vascular leak, and pathogens such as anthrax, the H1N1 flu virus, SARS, or the Hanta virus, pulmonary and other types of Acute Lung Injury/Acute Respiratory Stress Syndrome (ALI/ARDS), fibrosis, and lung injury in general. The present disclosure is not limited to a particular mechanism. Indeed, an understanding of the mechanism is not necessary to practice the present disclosure. Nonetheless, one mechanism that has been suggested to explain vascular leak and edema in high altitude is a direct effect of hypoxia on endothelial cells.

The pharmaceutical compositions may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

In some embodiments, the present disclosure provides MK2 activators, as described herein, in combination with an additional agent (e.g., another agent useful for activating MK2, augmenting permeability barriers, such as epithelial and/or endothelial barriers, and/or treating diseases, conditions, disorders, and/or injuries associated therewith, such as edema and other barrier diseases and injuries). In some embodiments, therapeutic compositions of embodiments of the present disclosure are administered in combination with agents that cause or exacerbate an edema as an undesired side effect, in order to prevent or reduce the edema. Additional agents include, but are not limited to, preload reducers (e.g., agents that decrease the pressure caused by fluid going into the heart and lungs; includes nitroglycerin and diuretics, such as furosemide (Lasix)), morphine (Astramorph, Roxanol), afterload reducers (e.g., agents that dilate blood vessels and take a pressure load off the heart's left ventricle; includes nitroprusside (Nitropress), enalapril (Vasotec) and captopril (Capoten)), blood pressure medications (lisinopril and the like), and acetazolamide (Diamox). ALI/ARDS is often accompanied by pneumonia, so MK2 activators can be combined with antibiotics.

The present disclosure also provides drug screening assays (e.g., to screen for drugs useful in treating pulmonary edema or other disorders or the lung or blood brain barriers). The screening methods utilize MK2 or signaling partners thereof. For example, in some embodiments, methods of screening for compounds that alter (e.g., increase) the expression or activity of MK2 are provided. The compounds or agents may interfere with transcription, by interacting with, for example, the promoter region. The compounds or agents may interfere with mRNA produced from a MK2 modulator (e.g., by RNA interference, antisense technologies, etc.). The compounds or agents may interfere with pathways that are upstream or downstream of the biological activity of MK2. In some embodiments, candidate compounds are antisense or interfering RNA agents (e.g., oligonucleotides) directed against MK2 modulators. In other embodiments, candidate compounds are antibodies, peptides, peptidomimetics or small molecules that enhance MK2 activity.

In one screening method, candidate compounds are evaluated for their ability to alter MK2 modulator expression by contacting a compound with a cell expressing a MK2 modulator then assaying for the effect of the candidate compounds on expression. In some embodiments, the effect of candidate compounds on expression of a gene is assayed for by detecting the level of gene specific mRNA expressed by the cell. mRNA expression can be detected by any suitable method.

In other embodiments, the effect of candidate compounds on expression of a gene is assayed by measuring the level of polypeptide encoded by the gene. The level of polypeptide expressed can be measured using any suitable method, including but not limited to, those disclosed herein.

Specifically, the present disclosure provides screening methods for identifying modulators, i.e., candidate or test compounds or agents (e.g., proteins, peptides, peptidomimetics, peptoids, small molecules or other drugs) which bind to MK2 or MK2 modulators, have an inhibitory (or stimulatory) effect on, for example, MK2 expression or activity, or have a stimulatory or inhibitory effect on, for example, the expression or activity of a MK modulator or substrate. Compounds thus identified can be used to modulate the activity of target gene products either directly or indirectly in a therapeutic protocol, to elaborate the biological function of the target gene product, or to identify compounds that disrupt normal target gene interactions. Compounds that enhance the activity or expression of MK2 are useful in the treatment of disorders or lung blood brain barriers, e.g., pulmonary edema, or other diseases, conditions, disorders, and/or injuries disclosed herein.

In one embodiment, the disclosure provides assays for screening candidate or test compounds that are substrates of a MK2 protein or polypeptide or a biologically active portion thereof. In another embodiment, assays for screening candidate or test compounds that bind to or modulate the activity of a MK2 protein or polypeptide or a biologically active portion thereof are provided.

The test compounds can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem., 1994, 37, 2678-85); spatially addressable parallel solid phase or solution phase libraries; synthetic library methods requiring deconvolution; the "one-bead one-compound" library method; and synthetic library methods using affinity chromatography selection. The biological library and peptoid library approaches are suitable for use with peptide libraries, while the other four approaches are applicable to peptide, non-peptide oligomer or small molecule libraries of compounds (Lam, Anticancer Drug Des., 1997, 12, 145).

Examples of methods for the synthesis of molecular libraries can be found in the art, for example in: DeWitt et al., Proc. Natl. Acad. Sci. USA, 1993, 90, 6909; Erb et al., Proc. Nad. Acad. Sci. USA, 1994, 91, 11422; Zuckermann et al., J. Med. Chem., 1994, 37, 2678; Cho et al., Science, 1993, 261, 1303; Carrell et al., Angew. Chem. Int. Ed. Engl., 1994, 33, 2059; Carell et al., Angew. Chem. Int. Ed. Engl., 1994, 33, 2061; and Gallop et al., J. Med. Chem., 1994, 37, 1233.

Libraries of compounds may be presented in solution (e.g., Houghten, Biotechniques, 1992, 13, 412-421), or on beads (Lam, Nature, 1991, 354, 82-84), chips (Fodor, Nature, 1993, 364, 555-556), bacteria or spores (U.S. Pat. No. 5,223,409, plasmids (Cull et al., Proc. Nad. Acad. Sci. USA, 1992, 89, 1865-1869) or on phage (Scott et al., Science, 1990, 249, 386-390; Devlin, Science, 1990, 249, 404-406; Cwirla et al., Proc. Natl. Acad. Sci., 1990, 87, 6378-6382; and Felici, J. Mol. Biol., 1991, 222, 301).

Accordingly, embodiments of the present disclosure provide agents that activate MK2 signaling for use in research, screening and therapeutic applications.

Figure 6:
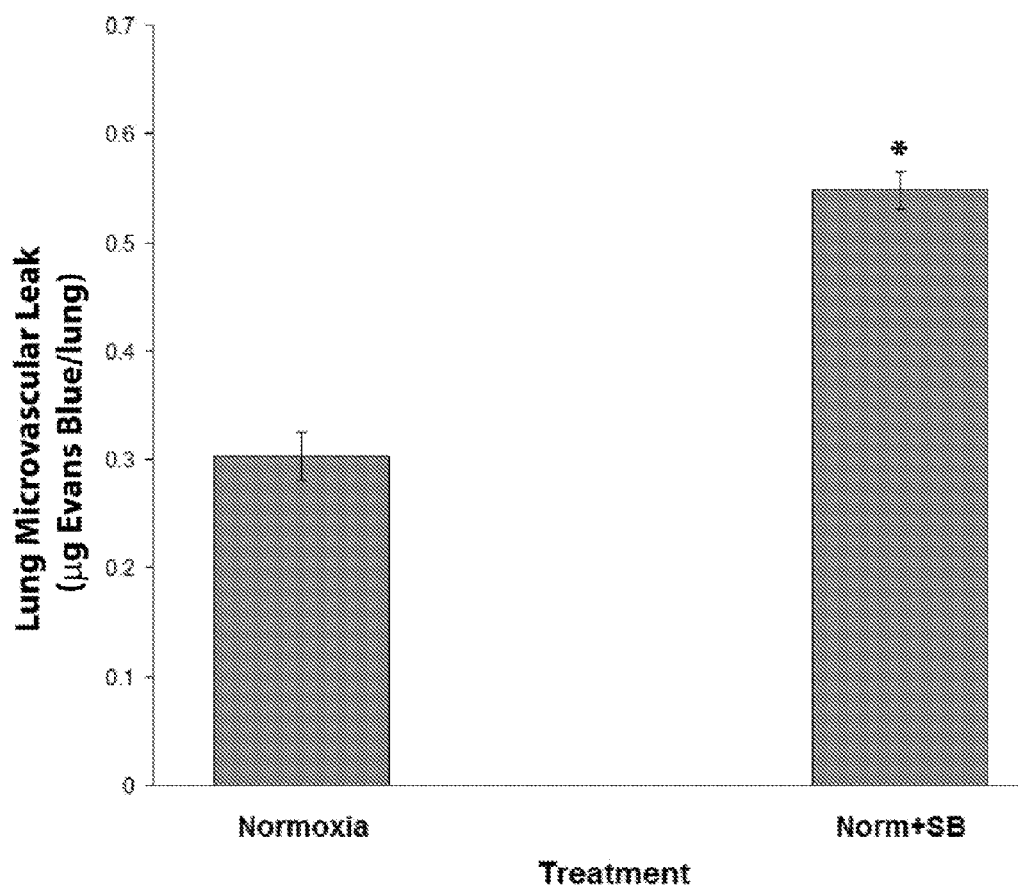
FIG. 6 shows that inhibition of p38 increases vascular leak in the lungs of rats.
Figure 7:
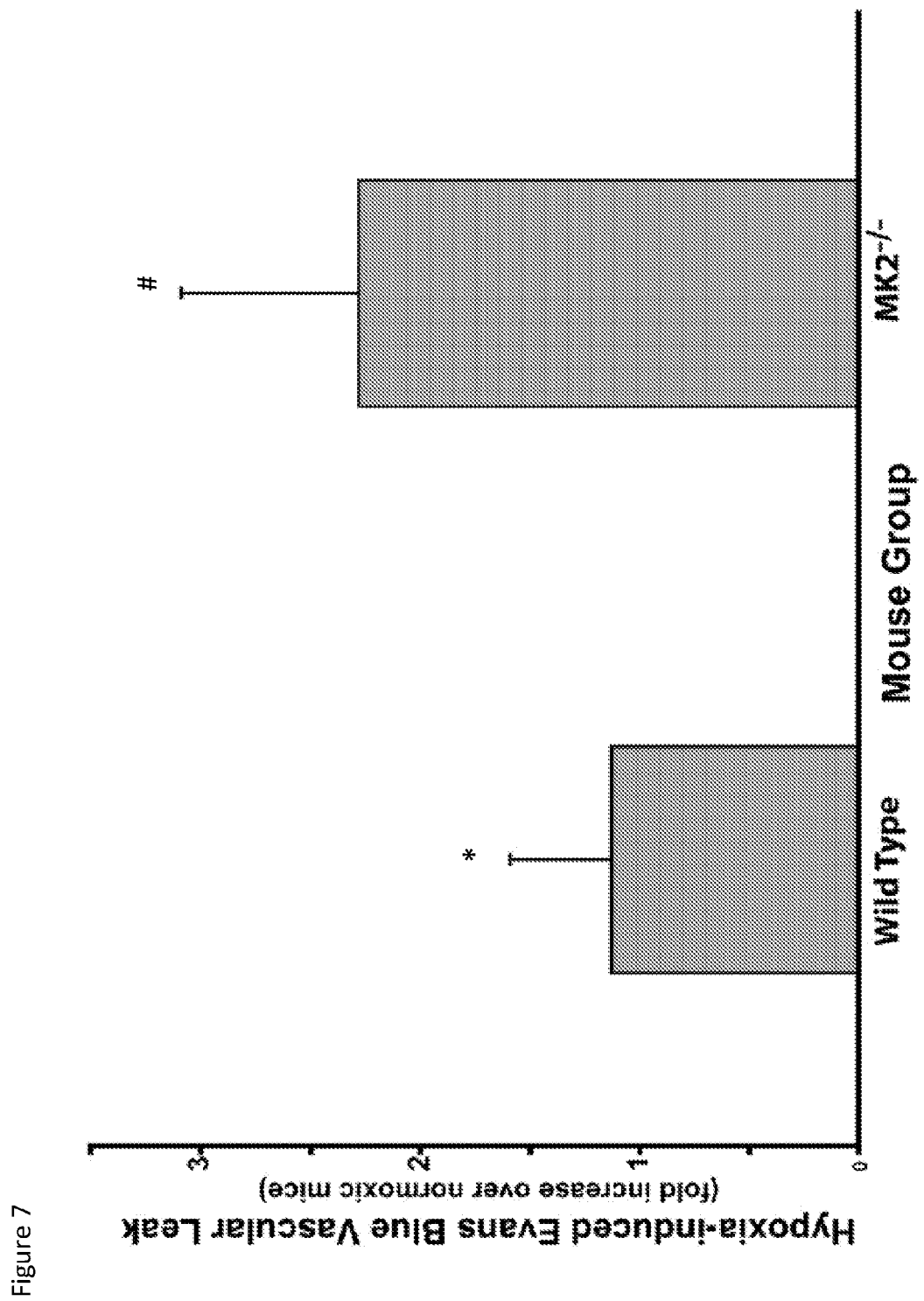
FIG. 7 shows that MK2−/− mice are more susceptible to hypoxia-induced pulmonary edema.

Treatment of rats with the p38 inhibitor SB203580 (1 μmol/kg) caused an increase in leak of intravenously injected Evans Blue into their lungs (see, FIG. 6). MK2 knockout (MK2−/−) mice (Liu et al., Am. J. Respir. Cell. Mol. Biol., 2007, 37, 507-517), had a leakier barrier than wild type mice in response to hypoxia (see, FIG. 7) and bleomycin treatment.

Figure 8:
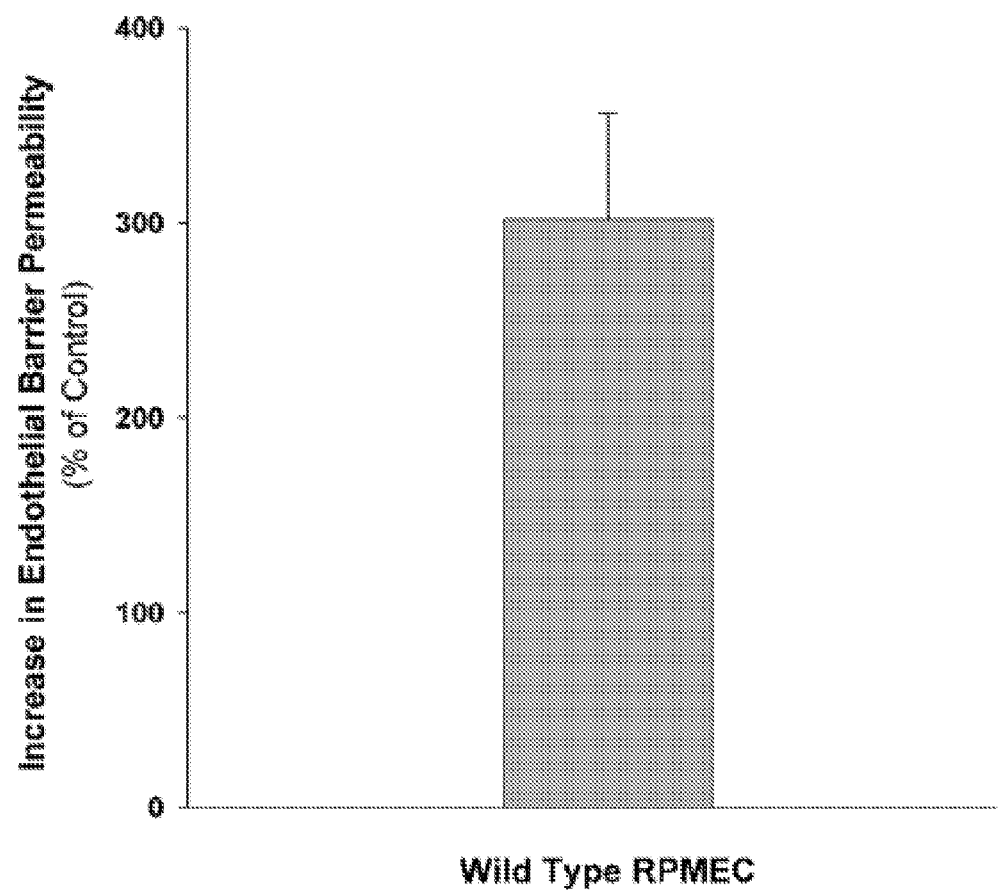
FIG. 8 shows that LeTx induces permeability and gap formation in wild type RPMEC.
Figure 9:
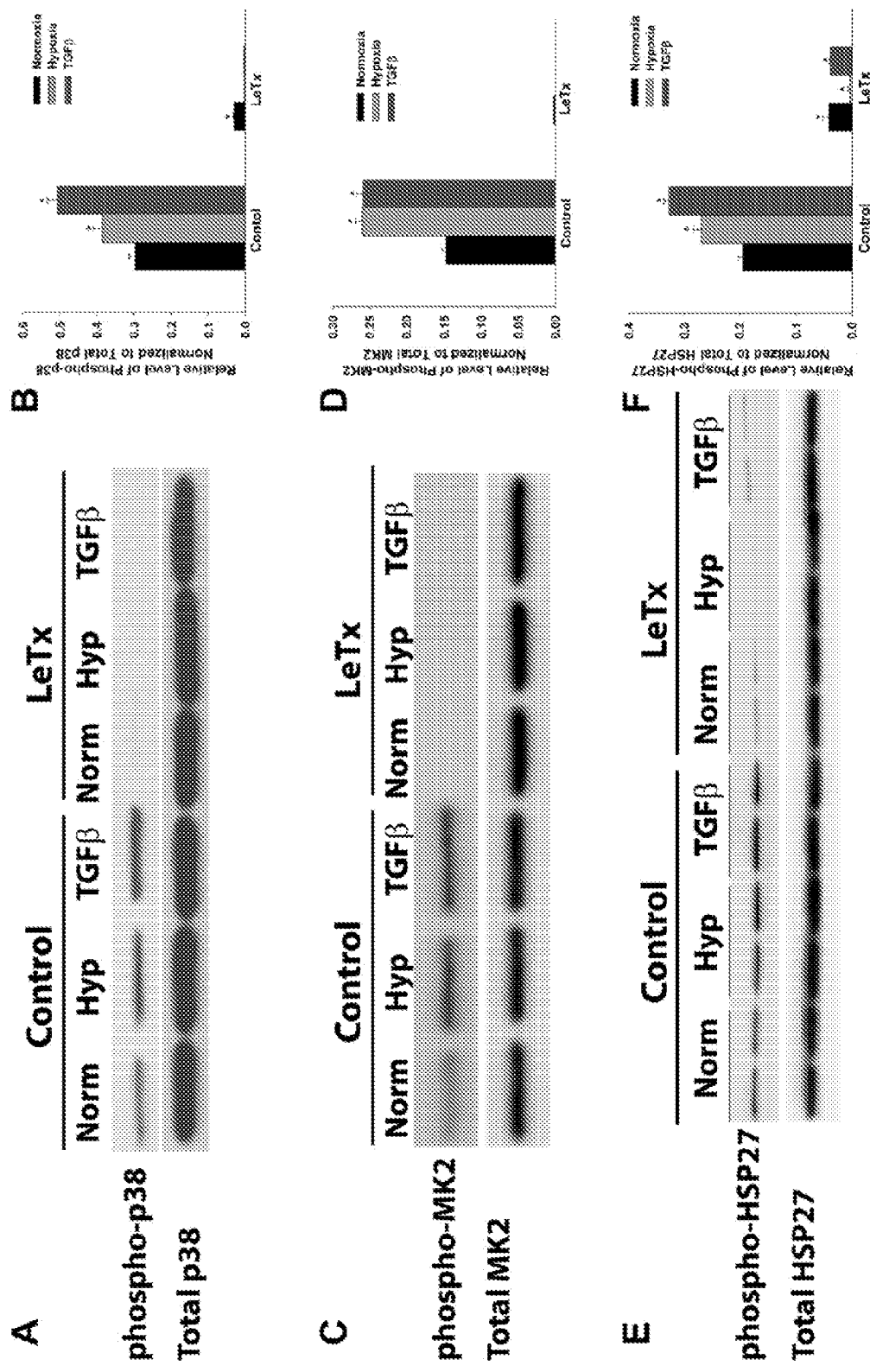
FIG. 9 shows that LeTx reduces phosphorylation of p38, MK2 and HSP27 in RPMEC.
Figure 10:
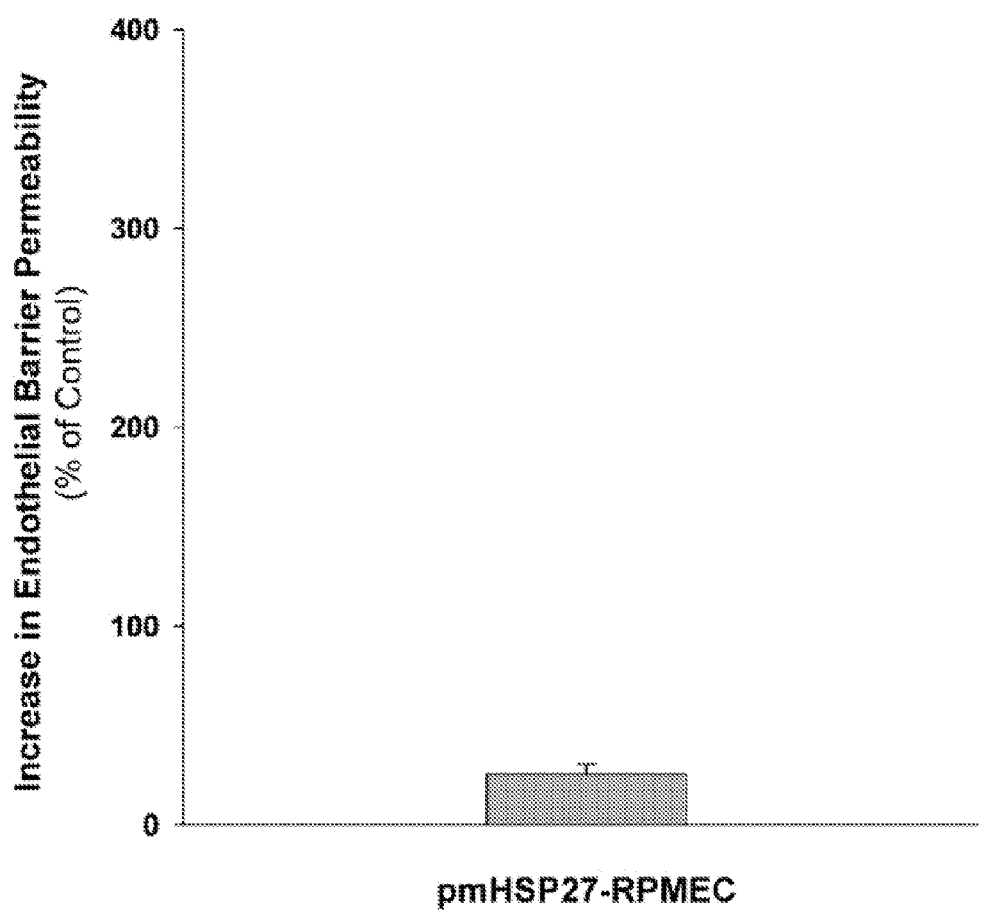
FIG. 10 shows that overexpressing pmHSP27 protects RPMEC from LeTx-induced permeability and gap formation.
Figure 11:
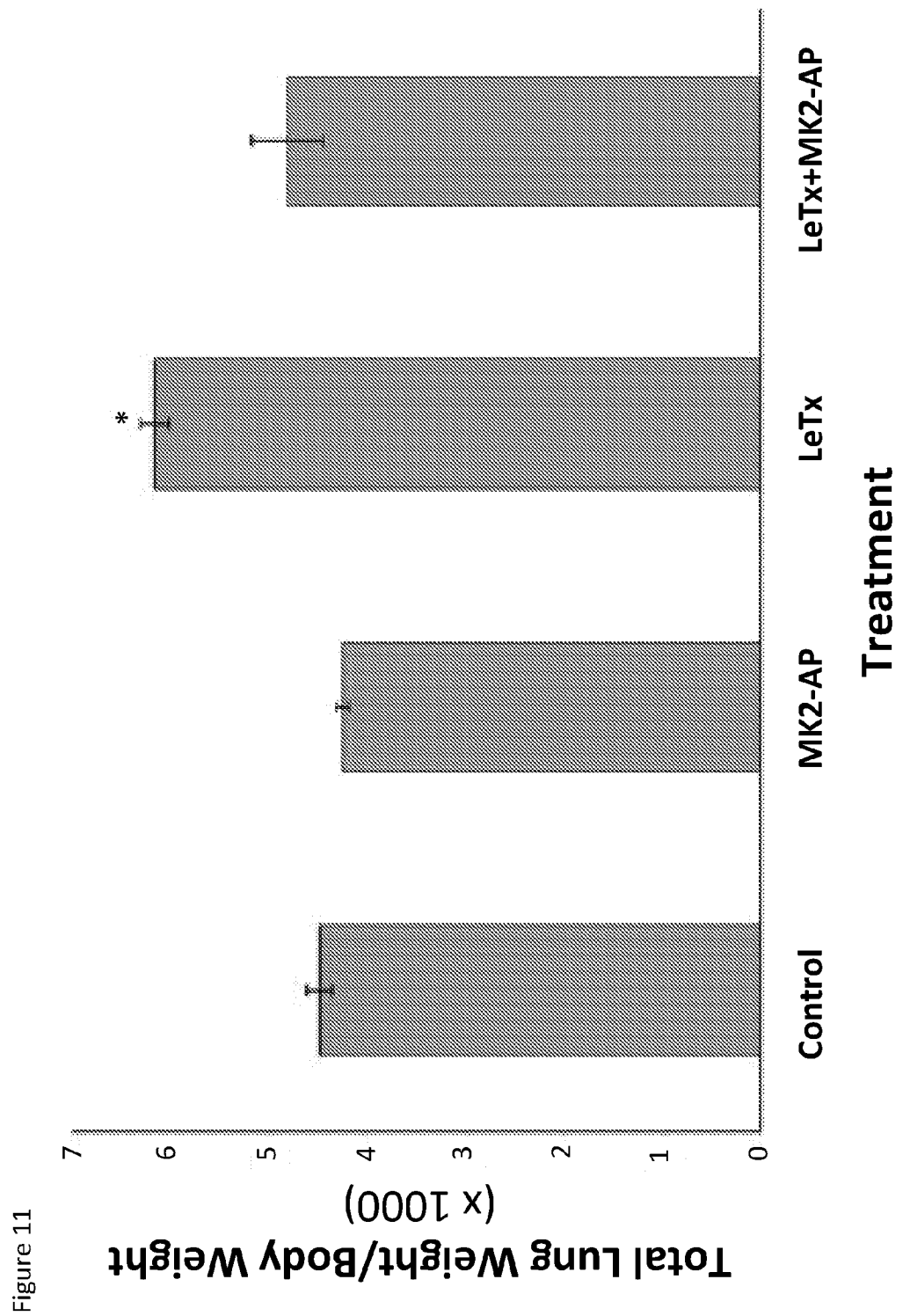
FIG. 11 shows LeTx increased lung weight relative to body weight, an effect which could be blocked by peptide.

LeTx treatment (2 μg/mL) increased the permeability of the endothelial monolayer barrier by 300% (see, FIG. 8). LeTx treatment also induced formation of gaps between endothelial cells that were virtually absent in control cells. LeTx treatment (2 μg/mL for 30 minutes) reduced p38 phosphorylation (activation) in RPMEC (see, FIG. 9). In addition, LeTx blocked the activation of p38 by agents previously described to activate p38 signaling in RPMEC (Liu et al., J. Cell. Physiol., 2009, 220, 600-610; and Liu et al., Am. J. Physiol. Cell Physiol., 2010, 299, C363-C373) such as hypoxia (3% $O_2$ for 1 hour) or TGFβ (1 ng/mL for 15 minutes). Furthermore, LeTx treatment blocked the phosphorylation (activation) of MK2 and its substrate HSP27 (see, FIG. 9) at baseline, or after activation with hypoxia or TGFβ. As shown in FIG. 8A, treatment of pmHSP27-RPMEC with LeTx (2 μg/mL) only caused insignificant increase (~25%) over control in the flux of 3 kDa alexafluor-488-dextran. Thus, compared to wild type RPMEC in which LeTx caused a 300% increase in permeability (see, FIG. 8A), pmHSP27-RPMEC appeared relatively resistant to its permeability inducing effect. Consistent with this finding, when pmHSP27-RPMEC was stained with the membrane fluorescent dye, it was observed that LeTx did not induce gap formation between endothelial cells (see, FIG. 10) as it did in wild type RPMEC (see, FIG. 8). These results indicate that overexpressing pmHSP27 in endothelial cells protects them against LeTx-induced permeability.

The present disclosure also provides any one or more of the foregoing compounds for activating MK2, augmenting permeability barriers, such as epithelial and/or endothelial barriers, and/or treating diseases, conditions, disorders, and/or injuries associated therewith.

The present disclosure also provides any one or more of the foregoing compounds for use in the manufacture of a medicament for activating MK2, augmenting permeability barriers, such as epithelial and/or endothelial barriers, and/or treating diseases, conditions, disorders, and/or injuries associated therewith.

The present disclosure also provides uses of any one or more of the foregoing compounds for activating MK2, augmenting permeability barriers, such as epithelial and/or endothelial barriers, and/or treating diseases, conditions, disorders, and/or injuries associated therewith.

The present disclosure also provides uses of any one or more of the foregoing compounds in the manufacture of a medicament for activating MK2, augmenting permeability barriers, such as epithelial and/or endothelial barriers, and/or treating diseases, conditions, disorders, and/or injuries associated therewith.

The present disclosure also provides any one or more of the foregoing compounds, or pharmaceutical compositions comprising the same, or methods of preparing the same, or methods of using the same, or uses any one or more of the foregoing compounds, substantially as described with reference to the accompanying examples and/or figures.

The present disclosure also provides methods of detecting MK2 activity in a cell. Any cell can be used, including RPMEC. The cell(s) is/are contacted with anthrax toxin, such as LeTx, in an amount such as, for example, 0.1 mg/mL to 20 mg/mL, or 2 mg/mL, for a duration of time, such as 1 minute to 1 hour. The cell(s) is/are then contacted with one or more amounts of a test compound, such as a compound suspected of activating MK2, or control compound (such as saline) for a duration of time, such as 1 minute to 30 minutes. The presence of phosphorylated HSP27, or other such substrate for MK2, is detected. Detection can be carried out, for example, by immunoblotting cell lysates with an antibody against phosphorylated HSP27 and, optionally, total HSP27. A greater amount of phosphorylated HSP27 in the presence of the test compound compared to the amount of phosphorylated HSP27 in the presence of anthrax toxin and control compound indicates that the test compound induces MK2 activity in the cell.

The present disclosure also provides methods of mimicking Acute Lung Injury (ALI) in a mammal in vivo. The resultant mammal thus serves as an in vivo animal model for ALI. In some embodiments, the mammal is administered an anthrax toxin (such as LeTx) for a period of time. A reason for administering the anthrax toxin is to create such an animal model. The anthrax toxin induces an increase in barrier leak in vasculature in the lungs of the mammal in vivo.

The present disclosure also provides methods of detecting a decrease in barrier leak in a mammal in vivo. The mammal (such as a rodent, for example, a rat or mouse) is administered a test compound, such as a compound suspected of activating MK2, or a control compound (such as saline) for a period of time, such as 1 minute to 30 minutes, or 15 minutes. Administration can be carried out by, for example, instilling a catheter through the jugular vein of the mammal. The mammal is then administered anthrax toxin, such as LeTx (such as 15 μg), for a period of time (such as 30 minutes and 60 minutes). Alternately, the mammal can be administered anthrax toxin followed by test compound or a control compound (e.g., the reverse order). In some embodiments, the mammal is then optionally administered the same test compound or a control compound for a period of time. A detectable reagent, such as a dye (such as Evans Blue dye, or the like), pigment, radiolabeled compound, or florescent compound is administered to the mammal (such as via the catheter), for example, after 60-120 minutes, or 90 minutes, from anthrax treatment. Lung tissue from the mammal is examined. The lung tissue can be obtained after sacrifice of the mammal (for example, after 20-40 minutes, or 30 minutes following administration of detectable reagent). Vascular leak and edema are reflected by the accumulation of the detectable reagent (i.e., Evans blue dye) which complexes with serum albumin into tissues where the permeability barrier is compromised. A decrease in the amount of the detectable reagent in the lung tissue from the mammal receiving the test compound and anthrax toxin compared to the amount of the detectable reagent in the lung tissue from the mammal receiving the anthrax toxin and the control compound, indicates that the test compound decreases barrier leak in a mammal in vivo.

The following examples are provided to demonstrate and further illustrate certain embodiments and aspects of the present disclosure and are not to be construed as limiting the scope thereof.

EXAMPLES

Example 1

MK2-Activating Peptide

MK2 is the immediate kinase that phosphorylates HSP27. A specific approach to bring about HSP27 phosphorylation was investigated. In particular, the Kaposin peptide was investigated and a region thereof was identified and coupled at its amino terminus with a transduction domain sequence to yield a peptide having the following amino acid sequence: YARAAARQARAHPRNPARRTPGTRRGAPAA (SEQ ID NO:8). This strategy was successful, as this peptide activated MK2 leading to increased phosphorylation of its substrate HSP27.

Data on the synthesis of the peptide are as follows: Comments MK2A1; Di sulfide Bonds: 0; Chemistry Fmoc; Sequence: [H]-Tyr-Ala-Arg-Ala-Ala-Ala-Arg-Gln-Ala-Arg-Ala-His-Pro-Arg-Asn-Pro-Ala-Arg-Arg-Thr-Pro-Gly-Thr-Arg-Arg-Gly-Ala-Pro-Ala-Ala-[NH$_2$]; (SEQ ID NO:8) Composition: $C_{134}H_{227}N_{59}O_{35}$; Molecular Weight 3224.6684; C-Terminal: NH$_2$; N-Terminal: H; # of Residues: 30; AA List: AA Count (Ala 10, Arg 8, Asn 1, Gln 1, Gly 2, His 1, Pro 4, Thr 2, Tyr 1); Chemistry Fmoc; Resin Type Amide Resin; Resin Subs. 0.66 mmol/g; Resin mmoles 0.100 mmol; Resin weight 0.152 grams; Blank Abs. 0.00 0; Sample Volume 5.0 mL Two batches of 93 and 100% purity by were tested by HPLC for activation of MK2 (see, FIG. 1). The absorption, metabolism, distribution and pharmacokinetic profile of MK2-activating peptide are determined by routine procedures known to those skilled in the art. Based on this profile and the efficacy in blocking anthrax LeTX effects, the structure of the peptide is optimized by altering the transduction domain or other residues that affect stability.

Example 2

Activity of the MK2-Activating Peptide

Dose Response of MK2-Activating Peptide

Figure 2:
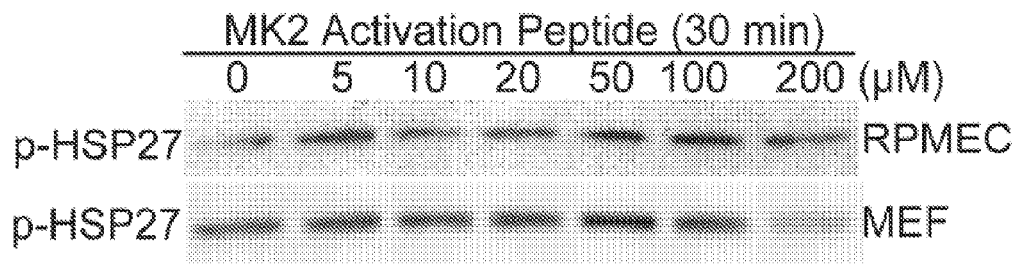
FIG. 2 shows dose response of MK-2 activating peptide of embodiments of the present disclosure.

Rat pulmonary endothelial cells (RPMEC) and mouse embryonic fibroblasts (MEF) were treated with increasing concentrations of MK2-activating peptide for 30 minutes. Cell lysates were immunoblotted with an antibody against phosphorylated HSP27 (reflects activity of MK2). As shown in FIG. 2, significant MK2 activation at 50 and 100 μM was observed.

Figure 3:
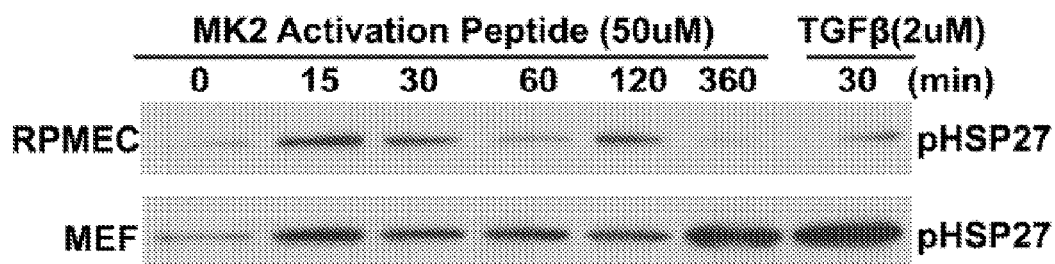
FIG. 3 shows a time course of MK2 activation by an MK-2 activating peptide of embodiments of the present disclosure.

Time-Course of MK2 Activation by MK2-Activating Peptide:

RPMEC and MEF were treated with 50 μM of MK2-activating peptide for a duration. Cell lysates were immunoblotted with an antibody against phosphorylated HSP27. TGFβ was used as a positive control that is known to activate p38-MK2-HSP27 signaling. As shown in FIG. 3, significant MK2 activation was observed by 15 minutes of treatment.

Figure 4:
FIG. 4 shows that MK2-activating peptide of embodiments of the present disclosure can reverse the effect of anthrax Lethal Toxin (LeTx) on activation of HSP27 phosphorylation.

MK2-Activating Peptide can Reverse the Effect of Anthrax LeTx on Activation of HSP27 Phosphorylation:

RPMEC were treated with anthrax LeTx (2 mg/mL) for a duration followed by treatment with 50 μM of MK2-activating peptide for 15 minutes. Cell lysates were immunoblotted with an antibody against phosphorylated HSP27 and total HSP27. As shown in FIG. 4, MK2-activating peptide was effective in reversing the effects of LeTx after 15 or 30 minutes (the point at which HSP27 phosphorylation was completely inhibited). MK2 activating peptide had no effect on the total level of HSP27 level, supporting its role in MK2 activation.

Figure 5:
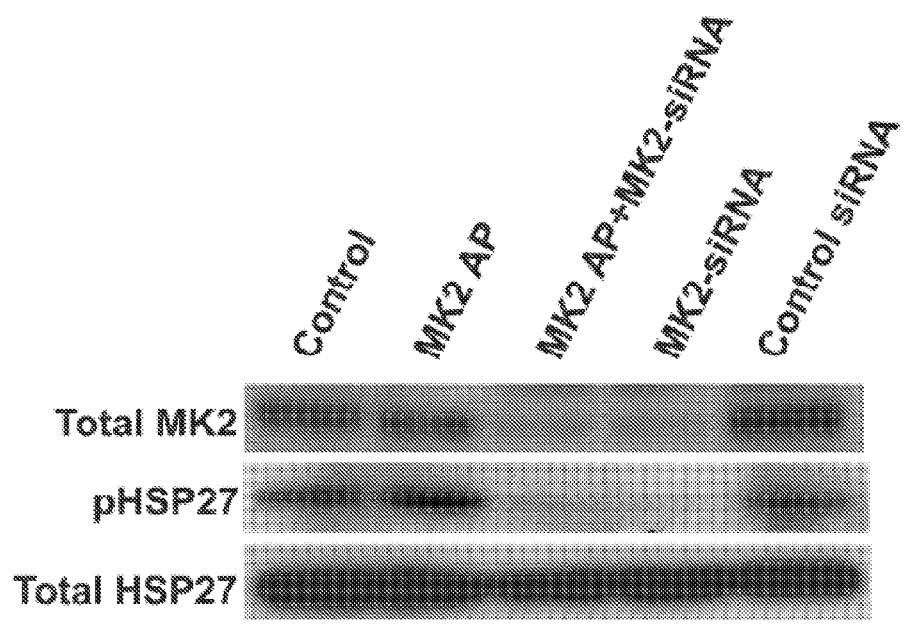
FIG. 5 shows that MK2-activating peptide effects on HSP27 phosphorylation can be blocked by knocking down MK2.

MK2-Activating Peptide Effects on HSP27 Phosphorylation can be Blocked by Knocking Down MK2:

RPMEC were treated with siRNA against MK2 which have previously been shown to be effective in knocking down MK2 (Allen et al., Stroke, 2010, 41, 2056-2063) or with control siRNA. As shown in FIG. 5, MK2 siRNA reduced the level of MK2 in the cells and blocked the activity of the MK2-activating peptide, indicating that it acts through MK2.

MK2-Activating Peptide can Block the Vascular Leak in Rats Treated with Anthrax Lethal Toxin LeTx:

Rats (~200 g) were instilled with a catheter through the jugular vein and treated with saline or 1.61 mg MK2-activating peptide in 300 μL saline. After 15 minutes, the rats were treated with 15 μg anthrax LeTx in 300 μL saline. After 30 minutes and 60 minutes from LeTx treatment, the rats were again treated with saline or 1.61 mg MK2-activating peptide (SEQ ID NO:8) in 300 μL saline. After 90 minutes from anthrax treatment, Evans Blue dye was injected through the catheter, and 30 minutes following that treatment, rats were sacrificed and their lungs removed. Vascular leak and edema are reflected by the accumulation of Evans blue dye which complexes with serum albumin into tissues where the permeability barrier is compromised. Rats treated with the anthrax LeTx alone had bluer lungs with several blue patches consistent with vascular leak and edema. In contrast, rats treated with MK2-activating peptide and anthrax LeTx had much clearer lungs, consistent with the ability of the MK2-activating peptide to block vascular leak.

Treatment of rats with the p38 inhibitor SB203580 (1 μmol/kg) caused an increase in leak of intravenously injected Evans Blue into their lungs (see, FIG. 6). MK2 knockout (MK2−/−) mice (Liu et al., Am. J. Respir. Cell. Mol. Biol., 2007, 37, 507-517), had a leakier barrier than wild type mice in response to hypoxia (see, FIG. 7) and bleomycin treatment.

LeTx treatment (2 μg/mL) increased the permeability of the endothelial monolayer barrier by 300% (see, FIG. 8). LeTx treatment also induced formation of gaps between endothelial cells that were virtually absent in control cells. LeTx treatment (2 μg/mL for 30 minutes) reduced p38 phosphorylation (activation) in RPMEC (see, FIG. 9). In addition, LeTx blocked the activation of p38 by agents previously described to activate p38 signaling in RPMEC (Liu et al., J. Cell. Physiol., 2009, 220, 600-610; and Liu et al., Am. J. Physiol. Cell Physiol., 2010, 299, C363-C373) such as hypoxia (3% $O_2$ for 1 hour) or TGFβ (1 ng/mL for 15 minutes). Furthermore, LeTx treatment blocked the phosphorylation (activation) of MK2 and its substrate HSP27 (see, FIG. 9) at baseline, or after activation with hypoxia or TGFβ. As shown in FIG. 8A, treatment of pmHSP27-RPMEC with LeTx (2 μg/mL) only caused insignificant increase (~25%) over control in the flux of 3 kDa alexafluor-488-dextran. Thus, compared to wild type RPMEC in which LeTx caused a 300% increase in permeability (see, FIG. 8A), pmHSP27-RPMEC appeared relatively resistant to its permeability inducing effect. Consistent with this finding, when pmHSP27-RPMEC was stained with the membrane fluorescent dye, it was observed that LeTx did not induce gap formation between endothelial cells (see, FIG. 10) as it did in wild type RPMEC (see, FIG. 8). These results indicate that overexpressing pmHSP27 in endothelial cells protects them against LeTx-induced permeability.

To further quantify permeability and vascular leak, lung weights among the different treatment groups were compared which, when normalized to body weights, is another measure of vascular leak and lung injury. As shown in FIG. 11, anthrax LeTx increased the lung weight/body weight significantly, while peptide had no significant effect on that ratio. Right and left lungs were weighed and divided by body weight for each rat and the average for each group compared. Furthermore, peptide treatment blocked the anthrax LeTx-induced increase in lung weight, which is consistent with its effect on Evans Blue accumulation.

Since increased actin stress fiber formation has been reported to reflect increased contractility and to be associated with increased endothelial barrier permeability in response to several agents, one skilled in the art would have expected RPMEC overexpressing pmHSP27 (pmHSP27-RPMEC) to form a weaker permeability barrier. Yet when pmHSP27-RPMEC were exposed to hypoxia they were surprisingly resistant to its permeability enhancing effect. TGFβ, another agent which induces permeability (Goldberg et al., Am. J. Physiol. Lung Cell. Mol. Physiol., 2002, 282, L146-154; Lee et al., Am. J. Respir. Cell. Mol. Biol., 2007, 37, 485-493; and Lu et al., J. Appl. Physiol., 2006, 101, 375-384) also failed to increase endothelial permeability in pmHSP27-RPMEC. Both hypoxia and TGFβ (1 ng/ml) increased permeability of wild type RPMEC. pmHSP27-RPMEC monolayers also contained significantly less and smaller intercellular gaps than wild type.

The MK2-activating peptide was shown to activate the p38-MK2-HSP27 pathway at multiple levels. The MK2-activating peptide specifically activates MK2 without noticeable cell toxic effects at the different levels investigated. This activation also occurred in pulmonary endothelial cells that were treated with anthrax LeTx indicating that it can be effective in reversing its effects on that signaling phase. Knocking down MK2 with siRNA blocks the effects of the drug on HSP27 phosphorylation indicating that its effects are specific. The peptide was also tested on mouse embryonic fibroblasts (MEF) and it was shown that it activates MK2 in these cells as well.

The MK2-activating peptide was not shown to affect other cellular processes and is also not expected to have off target effects. The MK2-activating peptide has the properties of specific targeting of MK2, the immediate activator of HSP27. The peptide is designed to be small, and in some embodiments has been combined with a sequence that makes its entry into the cell easier.

All publications and patents mentioned in the above specification are herein incorporated by reference. Various modifications and variations of the described method and system of the present disclosure will be apparent to those skilled in the art without departing from the scope and spirit of the disclosure. Although the present disclosure has been described in connection with specific embodiments, it should be understood that the subject matter as claimed should not be unduly limited to such specific embodiments. Indeed, various modifications of the described modes for carrying out the disclosure that are obvious to those skilled in the relevant fields are intended to be within the scope of the following claims.

What is claimed is:

1. A peptide comprising a transduction domain and a domain that blocks an autoinhibitory domain of Mitogen-Activated Protein Kinase-Activated Protein Kinase 2 (MK2), wherein the amino acid sequence of said peptide is at least 90% identical to YARAAARQARAHPRNPARRTPGTRRGAPAA (SEQ ID NO:8), YARKARRQARRHPRNPARRTPGTRRGAPAA (SEQ ID NO:9), YGRKKRRQRHPRNPARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTRRGAPAA (SEQ ID NO:12), or RRRRRRRRRHPRNPARRTPGTRRGAPAA (SEQ ID NO:13).

2. The peptide of claim 1, wherein the peptide comprises an amino acid sequence which is YARAAARQARAHPRNPARRTPGTRRGAPAA (SEQ ID NO:8), YARKARRQARRHPRNPARRTPGTRRGAPAA (SEQ ID NO:9), YGRKKRRQRHPRNPARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTRRGAPAA (SEQ ID NO:12), or RRRRRRRRRHPRNPARRTPGTRRGAPAA (SEQ ID NO:13).

3. The peptide of claim 1, wherein at least one L-amino acid is replaced with a D-amino acid.

4. The peptide of claim 1, wherein the peptide is cyclized.

5. A method of activating MK2 in a subject comprising administering to the subject a peptide comprising a transduction domain and a domain that blocks an autoinhibitory domain of MK2, wherein the amino acid sequence of said peptide is at least 90% identical to YARAAARQARAHPRNPARRTPGTRRGAPAA (SEQ ID NO:8), YARKARRQARRHPRNPARRTPGTRRGAPAA (SEQ ID NO:9), YGRKKRRQRHPRNPARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTRRGAPAA (SEQ ID NO:12), or RRRRRRRRRHPRNPARRTPGTRRGAPAA (SEQ ID NO:13).

6. A method of treating a subject having a disease, condition, disorder, or injury associated with an epithelial and/or an endothelial barrier comprising administering to a subject a peptide of claim 1 comprising a transduction domain and a domain that blocks an autoinhibitory domain of MK2, wherein the amino acid sequence of said peptide is at least 90% identical to
YARAAARQARAHPRNPARRTPGTRRGAPAA (SEQ ID NO:8),
YARKARRQARRHPRNPARRTPGTRRGAPAA (SEQ ID NO:9),
YGRKKRRQRHPRNPARRTPGTRRGAPAA (SEQ ID NO: 10),
YGRKKRRQRRRHPRNPARRTPGTRRGAPAA (SEQ ID NO: 11),
GRKKRRQRRRPPQCHPRNPARRTPGTRRGAPAA (SEQ ID NO: 12), or
RRRRRRRRRHPRNPARRTPGTRRGAPAA (SEQ ID NO: 13), wherein the disease, condition, disorder or injury is edema, a wound, a lung disease, chronic fatigue syndrome, acute mountain sickness (AMS), high altitude-related vascular leak or caused by anthrax bacteria.

7. The method of claim 6 wherein the edema is a pulmonary edema or cerebral edema.

8. The method of claim 7 wherein the edema is high altitude pulmonary edema (HAPE) or high altitude cerebral edema (HACE).

9. The method of claim 6 wherein the disease, condition, disorder or injury is caused by anthrax bacteria.

10. The method of claim 6 wherein the lung disease is pulmonary fibrosis.

11. The method of claim 5, wherein the peptide comprises an amino acid sequence which is YARAAARQARAHPRNPARRTPGTRRGAPAA (SEQ ID NO:8), YARKARRQARRHPRNPARRTPGTRRGAPAA (SEQ ID NO:9), YGRKKRRQRHPRNPARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTRRGAPAA (SEQ ID NO:12), or RRRRRRRRRHPRNPARRTPGTRRGAPAA (SEQ ID NO:13).

12. The method of claim 6, wherein the peptide comprises an amino acid sequence which is YARAAARQARAHPRNPARRTPGTRRGAPAA (SEQ ID NO:8), YARKARRQAR- RHPRNPARRTPGTRRGAPAA (SEQ ID NO:9), YGRKKRRQRHPRNPARRTPGTRRGAPAA (SEQ ID NO:10), YGRKKRRQRRRHPRNPARRTPGTRRGAPAA (SEQ ID NO:11), GRKKRRQRRRPPQCHPRNPARRTPGTRRGAPAA (SEQ ID NO:12), or RRRRRRRRRHPRNPARRTPGTRRGAPAA (SEQ ID NO:13).

\* \* \* \* \*

UNITED STATES PATENT AND TRADEMARK OFFICE
CERTIFICATE OF CORRECTION

PATENT NO. : 9,309,286 B2  
APPLICATION NO. : 14/239059  
DATED : April 12, 2016  
INVENTOR(S) : Usamah S. Kayyali Page 1 of 1

It is certified that error appears in the above-identified patent and that said Letters Patent is hereby corrected as shown below:

IN THE SPECIFICATION

Column 1, lines 17-20 should read:

"STATEMENT REGARDING FEDERALLY SPONSORED RESEARCH OR DEVELOPMENT

This invention was made with government support under grants DE016859, HL079320, and AI096087 awarded by the National Institutes of Health. The government has certain rights in the invention."

Signed and Sealed this  
Twenty-first Day of June, 2016

Michelle K. Lee  
*Director of the United States Patent and Trademark Office*